(12) United States Patent
Cimino et al.

(10) Patent No.: US 12,275,931 B2
(45) Date of Patent: Apr. 15, 2025

(54) ADIPOSE TISSUE PROCESSING METHOD

(71) Applicant: GID BIO, Inc., Louisville, CO (US)

(72) Inventors: William W. Cimino, Louisville, CO (US); Thomas Michael Johannsen, Centennial, CO (US); David Joe Wesley, Lyons, CO (US); Dale William Tomrdle, Louisville, CO (US)

( * ) Notice: Subject to any disclaimer, the term of this patent is extended or adjusted under 35 U.S.C. 154(b) by 0 days.

(21) Appl. No.: 18/212,506

(22) Filed: Jun. 21, 2023

(65) Prior Publication Data

US 2023/0332094 A1 Oct. 19, 2023

Related U.S. Application Data

(62) Division of application No. 16/630,762, filed as application No. PCT/US2018/014884 on Jan. 23, 2018, now Pat. No. 11,732,233.
(Continued)

(51) Int. Cl.
*C12M 3/00* (2006.01)
*B01L 3/00* (2006.01)
(Continued)

(52) U.S. Cl.
CPC ............ *C12M 45/09* (2013.01); *C12M 23/28* (2013.01); *C12M 23/44* (2013.01); *C12M 27/02* (2013.01);
(Continued)

(58) Field of Classification Search
CPC ....... C12M 27/10; C12M 27/02; C12M 45/09
See application file for complete search history.

(56) References Cited

U.S. PATENT DOCUMENTS 3,764,112 A 10/1973 Jelley
3,854,704 A 12/1974 Balas
(Continued)

FOREIGN PATENT DOCUMENTS

EP 0512769 A2 11/1992
JP 2009189282 A 8/2009
(Continued)

OTHER PUBLICATIONS

Fodor et al.; Adipose Derived Stromal Cell (ADSC) Injections for Pain Management of Osteoarthritis in the Human Knee Joint; Aesthtic Surgery Journal; 2016; vol. 36(2); pp. 229-236.
(Continued)

*Primary Examiner* — Nathan A Bowers
(74) *Attorney, Agent, or Firm* — HOLZER PATEL DRENNAN

(57) ABSTRACT

A tissue processing system for dissociation of and release of cellular components from adipose tissue to prepare stromal vascular fraction includes a portable tissue processing unit for containing biological material including adipose tissue during enzymatic digestion processing and a digestion drive unit configured to receive the tissue processing unit for rotational processing of the tissue processing unit about an axis of rotation. The unit has an upright orientation and a reclined orientation in which the axis of rotation is at a reclined angle to horizontal relative to the upright orientation. The digestion drive unit is configured to receive and drive rotation of the tissue processing unit in the reclined orientation. Methods for processing biological material including adipose tissue include enzymatically digesting adipose tissue with rotation of a tissue processing unit around an axis of rotation in a reclined orientation.

20 Claims, 16 Drawing Sheets

Related U.S. Application Data

(60) Provisional application No. 62/534,061, filed on Jul. 18, 2017.

(51) Int. Cl.
| | |
|---|---|
| *C12M 1/00* | (2006.01) |
| *C12M 1/06* | (2006.01) |
| *C12M 1/26* | (2006.01) |
| *C12M 3/04* | (2006.01) |

(52) U.S. Cl.
CPC ............ *C12M 27/10* (2013.01); *C12M 33/00* (2013.01); *C12M 33/14* (2013.01)

(56) References Cited

U.S. PATENT DOCUMENTS

| | | | |
|---|---|---|---|
| 4,223,094 A | 9/1980 | Vaseen | |
| 4,307,965 A | 12/1981 | Catarious et al. | |
| 4,438,032 A | 3/1984 | Golde et al. | |
| 4,820,626 A | 4/1989 | Williams et al. | |
| 5,035,708 A | 7/1991 | Alchas et al. | |
| 5,226,914 A | 7/1993 | Caplan et al. | |
| 5,299,864 A | 4/1994 | Reynolds et al. | |
| 5,330,914 A | 7/1994 | Uhlen et al. | |
| 5,336,616 A | 8/1994 | Livesey et al. | |
| 5,372,945 A | 12/1994 | Alchas et al. | |
| 5,409,833 A | 4/1995 | Hu et al. | |
| 5,443,438 A | 8/1995 | Wright et al. | |
| 5,486,359 A | 1/1996 | Caplan et al. | |
| 5,586,732 A | 12/1996 | Yamauchi et al. | |
| 5,591,625 A | 1/1997 | Gerson et al. | |
| 5,610,074 A | 3/1997 | Beritashvili et al. | |
| 5,624,418 A | 4/1997 | Shepard | |
| 5,624,840 A | 4/1997 | Naughton et al. | |
| 5,688,531 A | 11/1997 | Benayahu et al. | |
| 5,728,739 A | 3/1998 | Ailhaud et al. | |
| 5,736,396 A | 4/1998 | Bruder et al. | |
| 5,763,279 A | 6/1998 | Schwarz et al. | |
| 5,786,207 A | 7/1998 | Katz et al. | |
| 5,811,094 A | 9/1998 | Caplan et al. | |
| 5,816,702 A | 10/1998 | Mays et al. | |
| 5,817,050 A | 10/1998 | Klein | |
| 5,827,735 A | 10/1998 | Young et al. | |
| 5,827,740 A | 10/1998 | Pittenger | |
| 5,827,897 A | 10/1998 | Ailhaud et al. | |
| 5,854,292 A | 12/1998 | Ailhaud et al. | |
| 5,906,934 A | 5/1999 | Grande et al. | |
| 5,908,784 A | 6/1999 | Johnstone et al. | |
| 5,937,863 A | 8/1999 | Knowlton | |
| 5,968,356 A | 10/1999 | Morsiani et al. | |
| 6,200,606 B1 | 3/2001 | Peterson et al. | |
| 6,261,549 B1 | 7/2001 | Fernandez et al. | |
| 6,316,247 B1 | 11/2001 | Katz et al. | |
| 6,391,297 B1 | 5/2002 | Halvorsen | |
| 6,429,013 B1 | 8/2002 | Halvorsen et al. | |
| 6,478,966 B2 | 11/2002 | Zhou et al. | |
| 6,544,788 B2 | 4/2003 | Singh | |
| 6,555,374 B1 | 4/2003 | Gimble et al. | |
| 6,777,231 B1 | 8/2004 | Katz et al. | |
| 6,841,150 B2 | 1/2005 | Halvorsen et al. | |
| 6,852,533 B1 | 2/2005 | Rafii et al. | |
| 7,001,746 B1 | 2/2006 | Halvorsen et al. | |
| 7,033,587 B2 | 4/2006 | Halvorsen et al. | |
| 7,078,230 B2 | 7/2006 | Wilkison et al. | |
| 7,078,232 B2 | 7/2006 | Konkie et al. | |
| 7,179,649 B2 | 2/2007 | Halvorsen | |
| 7,266,457 B1 | 9/2007 | Hickman | |
| 7,294,334 B1 | 11/2007 | Michal et al. | |
| 7,347,391 B2 * | 3/2008 | Michalek | B09B 3/00 241/23 |
| 7,361,368 B2 | 4/2008 | Claude et al. | |
| 7,390,484 B2 | 6/2008 | Fraser et al. | |
| 7,429,488 B2 | 9/2008 | Fraser et al. | |
| 7,470,537 B2 | 12/2008 | Hedrick et al. | |
| 7,473,420 B2 | 1/2009 | Fraser et al. | |
| 7,501,115 B2 | 3/2009 | Fraser et al. | |
| 7,514,075 B2 | 4/2009 | Hedrick et al. | |
| 7,531,355 B2 | 5/2009 | Rodriguez et al. | |
| 7,572,236 B2 | 8/2009 | Quick et al. | |
| 7,582,292 B2 | 9/2009 | Wilkison et al. | |
| 7,585,670 B2 | 9/2009 | Hedrick et al. | |
| 7,595,043 B2 | 9/2009 | Hedrick et al. | |
| 7,622,108 B2 | 11/2009 | Collins et al. | |
| 7,641,643 B2 | 1/2010 | Michal et al. | |
| 7,651,684 B2 | 1/2010 | Hedrick et al. | |
| 7,659,118 B2 | 2/2010 | Furcht et al. | |
| 7,670,596 B2 | 3/2010 | Collins et al. | |
| 7,687,059 B2 | 3/2010 | Fraser et al. | |
| 7,708,152 B2 | 5/2010 | Dorian et al. | |
| 7,727,763 B2 | 6/2010 | McKenna, Jr. et al. | |
| 7,732,190 B2 | 6/2010 | Michal et al. | |
| 7,744,869 B2 | 6/2010 | Simon | |
| 7,749,741 B2 | 7/2010 | Bullen et al. | |
| 7,771,716 B2 | 8/2010 | Hedrick et al. | |
| 7,780,649 B2 | 8/2010 | Shippert | |
| 7,780,860 B2 | 8/2010 | Higgins et al. | |
| 7,789,872 B2 | 9/2010 | Shippert | |
| 7,794,449 B2 | 9/2010 | Shippert | |
| 7,887,795 B2 | 2/2011 | Fraser et al. | |
| 7,901,672 B2 | 3/2011 | Fraser et al. | |
| 8,366,694 B1 | 2/2013 | Jordan | |
| 9,206,387 B2 | 12/2015 | Llull et al. | |
| 9,260,697 B2 | 2/2016 | Cimino et al. | |
| 9,296,984 B2 | 3/2016 | Cimino et al. | |
| 9,907,883 B2 | 3/2018 | Llull et al. | |
| 9,909,094 B2 | 3/2018 | Cimino et al. | |
| 9,909,095 B2 | 3/2018 | Cimino et al. | |
| 9,950,015 B2 | 4/2018 | Cimino et al. | |
| 10,138,457 B2 | 11/2018 | Cimino et al. | |
| 10,336,980 B2 | 7/2019 | Cimino et al. | |
| 10,898,525 B2 | 1/2021 | Cimino et al. | |
| 11,261,418 B2 | 3/2022 | Cimino et al. | |
| 11,649,427 B2 | 6/2023 | Cimino et al. | |
| 2001/0030152 A1 | 10/2001 | Wright et al. | |
| 2001/0033834 A1 | 10/2001 | Wilkison et al. | |
| 2002/0076400 A1 | 6/2002 | Katz et al. | |
| 2002/0119126 A1 | 8/2002 | Halvorsen | |
| 2003/0082152 A1 | 5/2003 | Hedrick et al. | |
| 2003/0161817 A1 | 8/2003 | Young et al. | |
| 2003/0211602 A1 | 11/2003 | Atala | |
| 2004/0067218 A1 | 4/2004 | Casteilla et al. | |
| 2004/0097867 A1 | 5/2004 | Fraser et al. | |
| 2004/0171146 A1 | 9/2004 | Katz et al. | |
| 2005/0048034 A1 | 3/2005 | Fraser et al. | |
| 2005/0076396 A1 | 4/2005 | Katz et al. | |
| 2005/0153442 A1 | 7/2005 | Katz et al. | |
| 2005/0282275 A1 | 12/2005 | Katz et al. | |
| 2006/0051865 A1 | 3/2006 | Higgins et al. | |
| 2006/0240546 A1 | 10/2006 | Goodwin et al. | |
| 2007/0190520 A1 | 8/2007 | Wolf et al. | |
| 2007/0225665 A1 | 9/2007 | Perez-Cruet et al. | |
| 2008/0014181 A1 | 1/2008 | Ariff et al. | |
| 2008/0050275 A1 | 2/2008 | Bischof et al. | |
| 2008/0213742 A1 | 9/2008 | Asgari et al. | |
| 2008/0319417 A1 | 12/2008 | Quijano et al. | |
| 2009/0042267 A1 | 2/2009 | Park | |
| 2010/0055087 A1 | 3/2010 | Higgins et al. | |
| 2010/0285521 A1 | 11/2010 | Vossman et al. | |
| 2010/0285588 A1 | 11/2010 | Stubbers et al. | |
| 2011/0117650 A1 | 5/2011 | Riordan | |
| 2012/0003733 A1 | 1/2012 | Gueneron | |
| 2012/0214659 A1 | 8/2012 | Do et al. | |
| 2014/0356939 A1 | 12/2014 | Sugiura | |
| 2017/0022465 A1 | 1/2017 | Ho | |
| 2017/0145369 A1 | 5/2017 | Poggel et al. | |

FOREIGN PATENT DOCUMENTS

| | | | |
|---|---|---|---|
| JP | 2011125813 A | 6/2011 | |
| JP | 2013507983 A | 3/2013 | |
| WO | 2010100212 A1 | 9/2010 | |
| WO | 2011052946 A2 | 5/2011 | |

(56) References Cited

FOREIGN PATENT DOCUMENTS

| WO | 2012006587 A2 | 1/2012 |
|---|---|---|
| WO | 2013106655 A1 | 7/2013 |
| WO | 2014039697 A1 | 3/2014 |
| WO | 2014110448 A1 | 7/2014 |
| WO | 2015035221 A1 | 3/2015 |
| WO | 2019018002 A1 | 1/2019 |

OTHER PUBLICATIONS

Garza et al.; "Use of Autologous Adipose-Derived Stromal Vascular Fraction to Treat Osteoarthritis of the Knee: A Feasibility and Safety Study"; Journal of Regenerative Medicine; 2015; vol. 4:1; 6 pgs.

Koh et al.; "Infrapatellar fat pad-derived mesenchymal stem cell therapy for kneee osteoarthritis"; The Knee; 2012; vol. 19; pp. 902-907.

Koh et al.; "Clinical results and second-look arthroscopic findings after treatment with adipose-derived stem cells for knee osteoarthritis"; Knee Surgery, Sports Traumatology, Arthroscopy; 2013;+C178 vol. 23(5); pp. 1308-1316.

Koh et al.; "Mesenchymal Stem Cell Injections Improve Symptoms of Knee Osteoarthritis"; Arthroscopy: The Journal of Arhtroscopic and Related Surgery; 2013; vol. 29(4); pp. 748-755.

Michalek et al.; "Autologous adipose tissue-derived stromal vascular fraction cells applicaiton in patients with osteoarthritis"; Cell Transplantation; 2015; 36 pgs.

Pak; "Regeneration of human bones in hip osteonecrosis and human cartilage in knee osteoarthritis with autologous adipose-tissue-derived stem cells: a case series"; Journal of Medical Case Reports; 2011; vol. 5:296; 8 pgs.

Pak et al.; "Safety reporting on implantation of autologous adipose tissue-derived stem cells with platelet-rich plasma into human articular joints"; BMC Musculoskeletal Disorders; 2013; vol. 14;337; 8 pgs.

\* cited by examiner

ADIPOSE TISSUE PROCESSING METHOD

CROSS-REFERENCE TO OTHER APPLICATIONS

This application is a divisional of U.S. patent application Ser. No. 16/630,762 entitled ADIPOSE TISSUE DIGESTION SYSTEM AND TISSUE PROCESSING METHODS having a 371(c) date of Jan. 13, 2020, which is a U.S. national stage filing under the Patent Cooperation Treaty of international patent application no. PCT/US2018/014884 filed Jan. 23, 2018, which claims a benefit of U.S. provisional patent application No. 62/534,061 entitled ADIPOSE TISSUE DIGESTION SYSTEM AND TISSUE PROCESSING METHOD filed Jul. 18, 2017, and the entire contents of each of these patent applications are incorporated by reference herein for all purposes.

BACKGROUND

Adipose tissue is recognized as a promising source of stem cells with at least multi-potent differentiation potential. Lipoasperate obtained during a lipoplasty procedure, such as during lipo surgery, may be processed to prepare a so-called stromal vascular fraction (SVF) that is rich in leuko stromal vascular cells, which include stem cells. Processing to prepare SVF may include washing lipoasperate with saline solution, followed by enzymatic digestion of washed tissue, and centrifuging digested material to prepare SVF in the form of a centrifuged pellet. Stem cells and other cells in SVF may be used in a variety of therapy and research applications. For some therapeutic applications, the SVF or portions thereof is used directly for administration, and without a need to first multiply cell numbers through culturing. This makes possible a very quick treatment procedure that may be performed in a single patient visit during which biological material including adipose tissue is collected from the patient (e.g., lipoaspirate from a lipoplasty procedure) and processed to prepare SVF and a treatment formulation with SVF is administered to the patient. One example of such a procedure is administration of SVF material to joints for treatment of osteoarthritis.

Various processing approaches have been proposed for processing biological material with adipose tissue to prepare SVF in a sufficient quantity and within a processing time suitable for one-visit medical treatment procedures.

One general approach to processing adipose tissue to prepare SVF is to perform the processing in a permanent, integrated processing system with multiple, fluidly interconnected processing units each with a dedicated process vessel or vessels and related equipment to perform a particular processing operation in a processing sequence, and with transfer of biological material through fluid connections between the different dedicated processing vessels to advance the biological material being process through the processing sequence to prepare and recover SVF. Such integrated processing systems permit each of the different processing units, and the process vessel(s) within each processing unit, to be individually designed and optimized for performing the particular processing operation to which a processing unit is dedicated and conveniently permit incorporation of process automation and control features, such as for fluid handling and transfer between the processing vessels of the different processing units, for addition of processing reagents to process vessels and for monitoring of system performance. However, such integrated processing systems tend to be large and bulky, complex equipment systems and very expensive.

Another general approach to processing adipose tissue to prepare SVF is to perform one of more process steps of a processing sequence while the biological material being processed is retained in a single-use, portable container apparatus that is manually transported between different processing stations where different processing operations are performed on the biological material within the portable container apparatus. The portable container apparatus may advantageously be designed to operate with standard clinical laboratory equipment, which may be significantly less expensive than specialized equipment of an integrated processing system and such standard laboratory equipment need not necessarily be dedicated to use only for adipose tissue processing to prepare SVF. However, with the use of a portable container apparatus, design flexibility may not be as great as for dedicated units of an integrated processing system, because the design of the portable container apparatus is limited to a small form factor that must accommodate requirements of multiple different processing operations and must compatibly operate with standard laboratory equipment.

Regardless of processing approach, two important factors for accomplishing one-visit SVF medical treatment procedures are processing time to prepare SVF and SVF yield, both of which are highly dependent upon the enzymatic digestion portion of the tissue processing operation. During the enzymatic digestion, the adipose tissue is contacted with an enzyme (e.g., collagenase) that breaks down the structure of, or dissociates, the adipose tissue to release the SVF components. Continuing the digestion processing for a longer duration of time may tend to increase an average degree of adipose tissue dissociation with a corresponding increase in SVF yield, but excessively long times for digestion processing are incompatible with time constraints for a single-visit therapeutic treatment. To promote an increase in SVF yield in a shorter amount of time, both integrated system approaches and portable container apparatus approaches tend to subject the adipose/enzyme mixture to agitation during enzymatic digestion to enhance contact between adipose tissue and the enzyme to promote more uniform dissociation of adipose tissue in a shorter period of time. With integrated processing systems, agitation is designed into the system. With a portable container apparatus, one approach has been to agitate the apparatus on an orbital shaker. Although these prior processing approaches have accomplished a level of success in preparation of SVF in timeframes and quantities useful for one-visit SVF medical treatment procedures, still it is estimated that SVF yields per unit mass of adipose tissue processed tend to be low both in the context of dedicated integrated processing systems and processing using portable container apparatus, with a significant majority of the potential SVF not being recovered within a reasonable period of time. Low SVF yields per unit mass of adipose tissue processed leads to collection and processing of larger volumes of lipoaspirate from patients to prepare a sufficient total quantity of SVF for a medical treatment procedure. In addition to increased patient discomfort, the quantity of adipose tissue extraction required for a treatment procedure may be larger than is reasonably available from some populations of people. There is a significant need for improved processing of biological material containing adipose tissue that is quick, cost effective and provides a high yield of recoverable SFV per unit mass of adipose tissue that is processed.

SUMMARY

Even with extensive agitation of the contents in a portable container apparatus during normal enzymatic digestion processing, dissociation of adipose tissue has often not been uniformly to a degree adequate to uniformly release the cellular components of SVF throughout the adipose tissue mass, resulting in a significant loss of potential yield of SVF. Typical processing in a portable container apparatus has been to provide the enzyme in an aqueous medium to contact adipose tissue in a portable container apparatus, but the adipose tissue tends to be in a mass that is difficult to penetrate with the aqueous digestion medium in a manner to adequately and uniformly dissociate adipose tissue in the interior portion of an adipose tissue mass, and so a result of enzymatic digestion processing has often been that an extent of adipose tissue disassociation was relatively high near the edges of the adipose tissue mass and was much lower in interior portions of the adipose tissue mass, resulting in a loss of yield of SFV from the interior portions. However, it has been found that many of the advantages associated with use of a portable container apparatus to process adipose tissue to prepare SVF from adipose tissue, including low equipment cost and relatively uncomplicated processing, may be achieved along with a high yield per unit mass of adipose tissue by incorporating into the processing enzymatic digestion processing with the portable container apparatus in a reclined orientation and rotated about a reclined axis of rotation. Various aspects of this disclosure relate to systems and methods relating to such enzymatic digestion processing.

One aspect of this disclosure involves a tissue digestion system for dissociation of and release of cellular components from adipose tissue. The tissue digestion system includes a portable tissue processing unit for containing biological material including adipose tissue during enzymatic digestion processing to dissociate and release cellular material from the adipose tissue and a digestion drive unit configured to selectively receive the tissue processing unit in a reclined orientation to drive rotation of the tissue processing unit in the reclined orientation. More particularly, the portable tissue processing unit may include:

a portable tissue processing unit for containing biological material including adipose tissue during enzymatic digestion processing to dissociate and release cellular material from the adipose tissue, the tissue processing unit including a single-use processing container with an internal fluid containment space to contain biological material including adipose tissue during enzymatic digestion processing;
the tissue processing unit comprising:
an axis of rotation extending through the fluid container in a direction from a bottom of the container toward a top of the container, the tissue processing unit being rotatable about the axis of rotation to rotate the fluid container about the axis of rotation for rotational processing of contents in the internal fluid containment space during the enzymatic digestion processing;
a selectively sealable and un-sealable inlet port through the top of the container and in fluid communication with the internal fluid containment space;
an upright orientation for introducing biological material containing adipose tissue from outside of to inside of the internal fluid containment space through the inlet port;
a reclined orientation for performing the rotational processing, wherein in the reclined orientation the axis of rotation is at a reclined angle to horizontal relative to the upright orientation; and
at least one mixing blade disposed in the internal fluid containment space of the container to contact and mix contents within the internal fluid containment space during the rotational processing; and
a digestion drive unit configured to selectively receive the tissue processing unit in the reclined orientation to drive rotation of the tissue processing unit and the container in the reclined orientation about the axis of rotation to mix contents within the internal fluid containment space with the said at least one mixing blade during the rotational processing.

Other aspects of this disclosure involve methods for processing biological material including adipose tissue to dissociate and release cellular components from the adipose tissue.

In some method aspects of this disclosure, a method may include:
enzymatically digesting adipose tissue of the biological material in an internal fluid containment space of a portable, single-use container of a portable tissue processing unit in the presence of enzyme in the internal fluid containment space, wherein the tissue processing unit comprises:
an axis of rotation extending through the container in a direction from a bottom of the container toward a top of the container, the tissue processing unit and the container being rotatable about the axis of rotation for rotational processing of contents in the internal fluid containment space;
at least one selectively sealable and un-sealable inlet port through the top of the container and in fluid communication with the internal fluid containment space; and
an upright orientation and a reclined orientation, wherein in the reclined orientation the axis of rotation is at a reclined angle to horizontal relative to the upright orientation;
prior to the enzymatic digesting, the tissue processing unit is in the upright orientation; and
the enzymatically digesting comprises rotating the tissue processing unit and the container about the axis of rotation while the tissue processing unit is in the reclined orientation with the said inlet port sealed.

In some method aspects of this disclosure, a method may include:
disposing a process fluid mass in an internal fluid containment space of a portable, single-use container of a portable tissue processing unit, the process material mass comprising biological material including adipose tissue and enzyme for enzymatic digestion of the adipose tissue in an internal fluid containment space, wherein the tissue processing unit comprises at least one mixing blade disposed in the internal fluid containment space; and
after the disposing, enzymatically digesting the adipose tissue of biological material in the process material mass in the internal fluid containment space, the enzymatically digesting comprising:
mixing the process material mass within the internal fluid containment space, the mixing comprising moving a said mixing blade through periodically repeating mixing cycles in the internal fluid containment space to contact and mix the process fluid mass;

wherein during the mixing the process material mass is in an amount having a quiescent volume corresponding to a quiescent partial fill volume of the internal fluid containment space in a range of from 30 percent to 75 percent of a maximum fluid fill volume capacity of the internal fluid containment space with a quiescent headspace volume in the internal fluid containment space above the quiescent partial fill volume, wherein the quiescent headspace volume is in a range of from 25 percent to 75 percent of the maximum fluid fill volume capacity of the internal fluid containment space; and wherein each said mixing cycle comprises moving at least a portion of the said mixing blade sequentially through the quiescent partial fill volume and the quiescent headspace volume.

A number of feature refinements and additional features are applicable to any one or more of these or other aspects of the disclosure. These feature refinements and additional features may be used individually or in any combination within the subject matter of any such aspects. As such, each of the following features may be, but are not required to be, used with any other feature or combination of features in relation to the same aspect or any other aspect of the disclosure.

In the reclined orientation, the axis of rotation may be inclined relative to horizontal at an angle of inclination in a range or from 0° to 45°. Some preferred ranges for the angle of inclination of the axis of rotation relative to horizontal in the reclined orientation with a lower limit of 0° include 0° to 40°, 0° to 35°, 0° to 30°, 0° to 25°, 0° to 20°, 0° to 15°, 0° to 12°, 0° to 10° and 0° to 8°. Some preferred ranges for the angle of inclination of the axis of rotation relative to horizontal in the reclined orientation with a lower limit of 1° include 1° to 45°, 1° to 40°, 1° to 35°, 1° to 30°, 1° to 25°, 1° to 20°, 1° to 15°, 1° to 12°, 1° to 10° and 1° to 8°. Some preferred ranges for the angle of inclination of the axis of rotation relative to horizontal in the reclined orientation with a lower limit of 2° include 2° to 45°, 2° to 40°, 2° to 35°, 2° to 30°, 2° to 25°, 2° to 20°, 2° to 15°, 2° to 12°, 2° to 10°, and 2° to 8°. Some preferred ranges for the angle of inclination of the axis of rotation relative to horizontal in the reclined orientation with a lower limit of 3° include 3° to 45°, 3° to 40°, 3° to 35°, 3° to 30°, 3° to 25°, 3° to 20°, 3° to 15°, 3° to 12°, 3° to 10°, and 3° to 8°. Some preferred ranges for the angle of inclination of the axis of rotation relative to horizontal in the reclined orientation with a lower limit of 4° include 4° to 45°, 4° to 40°, 4° to 35°, 4° to 30°, 4° to 25°, 4° to 20°, 4° to 15°, 4° to 12°, 4° to 10°, and 4° to 8°. One particularly preferred range for the angle of inclination of the axis of orientation relative to horizontal in the reclined orientation is from 0° to 30° and more preferably from 0° to 15°. Another particularly preferred range for the angle of inclination of the axis of orientation relative to horizontal in the reclined orientation is from 2° to 30° and more preferably from 2° to 15°.

In the upright orientation, the axis of rotation may be inclined relative to horizontal at an angle of inclination of from 45° to 90°, 50° to 90°, 55° to 90°, 60° to 90°, 65° to 90°, 70° to 90°, 75° to 90°, 80° to 90° and 85 to 90°. A particularly preferred range for the angle of inclination of the axis of rotation relative to horizontal in the upright orientation is from 60° to 90° and more preferably from 75° to 90°. Even more preferred is for the angle of inclination of the axis of rotation relative to horizontal in the upright orientation to be 85° to 90°, and still more preferably at or very close to 90° (vertically-extending).

As used herein, angle of inclination of the axis of rotation refers to the relationship of the axis of rotation relative to a horizontal plane. Such an angle of inclination is without reference to the direction of inclination relative to horizontal and has a value of 0° (horizontally-extending), 90° (vertically-extending) or an acute angle between 0° to 90°. As will be appreciated, for convenience of reference such an angle of the axis of rotation relative to horizontal is referred to as an angle of inclination even though including a horizontally-extending axis of rotation (angle of inclination of 0°, with no slope relative to horizontal) and a vertically-extending axis of rotation (angle of inclination of 90°, with infinite slope relative to horizontal).

The digestion drive unit may beneficially have a design that includes a plurality of longitudinally-extending rotational drive members on which the tissue processing unit is supported in the reclined orientation when received by the digestion drive unit. Each such rotational drive member may be rotatable about a longitudinal axis of the respective rotational drive member to drive rotation of the tissue processing unit in the reclined orientation about the axis of rotation. For convenience and simplicity of design, the digestion drive unit may be designed for the tissue processing unit to be supported by the rotational drive members by simply resting on the rotational drive members when received in the reclined orientation, to be retained on the rotational drive members during the rotational processing by gravity and without a specific retaining mechanism. In this way, the tissue processing unit may conveniently be engaged with the digestion drive unit for rotational processing by simply placing the tissue processing unit on top of the rotational drive members in the reclined orientation and upon completion of enzymatic digestion the tissue processing unit may conveniently be disengaged from the digestion drive unit simply by lifting the tissue processing unit up and away from the rotational drive members. Typically, the digestion drive unit will include at least such two rotational drive members and preferably includes only two such rotational drive members. In one advantageous enhancement, a top end portion of the tissue processing unit as received in the reclined orientation by the digestion drive unit is not in contact with the digestion drive unit, and in a preferred implementation is disposed distally beyond a distal end of the rotational drive members. In this way, the top end portion of the tissue processing unit may avoid any contact with the digestion drive unit and may consequently avoid issues of potential lack of sterility of the surfaces of the digestion drive unit. Such a top end portion of the tissue processing unit may extend distally beyond the distal end of each such rotational drive member by a distance of at least 2 millimeters or at least 4 millimeters, to provide sufficient length for a person to grab the top end with sterile gloves to position the tissue processing unit on the rotational drive members and to remove the tissue processing unit from the rotational drive members without contacting the rotational drive members or other portions of the digestion drive unit.

In one enhancement, the tissue processing unit may include a portable container apparatus with the processing container and a protective processing sleeve in which the container apparatus may be removably received with a bottom of the container apparatus disposed inside of an toward the bottom of the processing sleeve and with the processing sleeve having an open top beyond which a top portion of the container apparatus projects when the tissue processing unit is in the upright orientation. The tissue processing unit may be in contact with the digestion drive unit only through surfaces of the processing sleeve, and in a further enhancement a top portion of the processing sleeve may also project distally beyond the distal end of the rotational drive members when the tissue processing unit is received by the digestion drive unit for rotational processing, further protecting the portable container apparatus and the processing container from contact with potentially non-sterile surfaces of the digestion drive unit. Such outside surfaces of the tissue processing unit may be on side portions of the tissue processing unit having a circular cross-section perpendicular to the axis of rotation. To facilitate easy placement and removal from the digestion drive unit, the top portion of the tissue processing unit may include a laterally-extending lip portion that is disposed distal of the distal ends of the rotational drive members when the tissue processing unit is received by the digestion drive unit for rotational processing such that the lip portion projects in a vertically overlapping manner with the distal ends of the rotational drive members. Such a lip portion may have a flanged structure projecting from a body portion of the tissue processing unit by a lateral projection distance of at least 1 millimeter, at least 2 millimeters or at least 3 millimeters. Such a lip portion may be provided on a top portion of the protective processing sleeve.

The portable container apparatus may have a lid that encloses the internal fluid containment space from above when the tissue processing unit is in the upright orientation and the lid may include a lip around a top portion of the container apparatus that projects above the top of the processing sleeve and that projects laterally to a side of a top edge of the processing sleeve, providing a convenient feature for a person wearing a sterile glove to grasp to remove the container apparatus from the sleeve, for example after completion of tissue processing in the container apparatus. As may be appreciated, references to top, bottom or lateral in relation to the tissue processing unit or a container apparatus of the tissue processing unit refer to features of the tissue processing unit or container apparatus as oriented when the tissue processing unit or container is in the upright orientation.

The digestion drive unit may include a rotational drive motor and a rotational drive connection between the rotational drive motor and one or more rotational drive members. The rotational drive connection may drive rotation of at least one of the rotational drive members about its respective longitudinal axis to in turn drive rotation of the tissue processing unit in the reclined orientation about the axis of rotation. In some preferred implementations, such a rotational drive connection is made between the rotational drive motor and at least two rotational drive members to drive rotation of at least two rotational drive members about their respective longitudinal axes. Such a rotational drive connection may be provided by a drive belt connected with a rotational output shaft of the rotational drive motor, such as through a rotational drive pulley.

The digestion drive unit may be configured to drive rotation of the tissue processing unit in the reclined orientation at a rotational speed of from 5 to 40 revolutions of the tissue processing unit per minute about the axis of rotation, and preferably from 10 to 35 revolutions per minute and more preferably from 10 to 30 revolutions per minute. The digestion drive unit may be manipulable between an off mode when the rotational drive motor is not operating to drive rotation of the rotational drive member and an on mode when the rotational drive motor is operating to drive rotation of one or more rotational drive members. Manipulation between the off mode and the on mode may be provided by an on-off switch. The digestion drive unit may be configured so that when the digestion drive unit is in the on mode, the rotational drive members are driven at a fixed rotational speed to drive rotation of the tissue processing unit at a set rotational speed within such a range. In an alternative configuration, the digestion drive unit may include a user-manipulable adjustment mechanism permitting a user to adjust the rotational speed of rotation of the rotational drive members to thereby adjust the rotational speed of the tissue processing unit received by the digestion drive unit. As a further enhancement, the adjustment mechanism may provide for adjustment within a set range of rotational speeds for rotation of the tissue processing unit and not permit adjustment outside of that range.

To assist both positive transmission of rotational drive energy to the tissue processing unit and prevention of migration of the tissue processing unit in the direction of a longitudinal axis of a rotational drive member, one or more of the rotational drive members may include a traction, or grip, feature that may extend circumferentially around the rotational drive member to engage and maintain enhanced frictional contact with the tissue processing unit during rotation of the tissue processing unit. The traction feature may be provided by a relatively soft material relative to a structural portion of the rotational drive member. For example, such a traction feature may be made of a material having a hardness in a range of from Shore A 30 to Shore A 90 durometer (and more preferably from Shore A 40 to Shore A 80 durometer), whereas a structural portion of the rotational drive member may be made of a much harder material of construction, such as of a metallic material or a hard engineering plastic. Such a traction feature may be made of an elastomeric material. A rotational drive member may include a single such traction feature, which in a preferred arrangement may be disposed adjacent a distal end of the rotational drive member, or may include multiple such traction features disposed at different longitudinal positions along the length of the rotational drive member.

The tissue processing unit includes at least one mixing blade disposed in the internal fluid containment space of the processing container to contact and mix contents within the internal fluid containment space during rotational processing, but may preferably include multiple mixing blades and may include multiple sets of mixing blades. Some or all of such mixing blades may be fixed in position relative to the container or may be movable relative to the container at some or all times. In some implementations, one or more mixing blades may be connected with a mixing shaft extending through a wall, preferably a top wall, of the processing container from outside of to inside of the internal fluid containment space. Such a mixing shaft may be rotatable relative to the processing container to rotate each mixing blade connected with the rotatable shaft through the internal fluid containment space. The tissue processing unit may include a hand-manipulable handle disposed outside of the internal fluid containment space and connected with the mixing shaft for hand-operation of the mixing shaft. In some preferred implementations, such a mixing shaft may be configured to be retained in a fixed relation relative to the processing container when the tissue processing unit is rotated by the digestion drive unit about the axis of rotation in the reclined orientation. Such a configuration permits the mixing shaft to be rotated relative to the processing container when convenient for processing with the tissue processing unit in the upright orientation, for example to mix wash liquid with lipoaspirate to wash the biological material in the internal fluid containment space prior to digestion processing. The processing container may have an internal filter disposed within the internal fluid containment space that divides the internal fluid containment space into a tissue retention portion disposed on one side of the filter and configured to receive a feed of biological material for processing through the inlet port and a filtrate portion disposed on opposing side of the filter to receive fluid passing from the tissue retention portion across the filter into the filtrate portion. The processing container may include a vacuum suction port in fluid communication with the filtrate portion suction liquid from the filtrate portion. One or more of the mixing blades may be disposed within the tissue retention portion to mix contents, including biological material, within the tissue retention portion during processing.

The tissue digestion system may include the tissue processing unit received in the digestion drive unit in the reclined orientation for rotational processing. The tissue digestion system may include a material mass disposed in the internal fluid containment space for enzymatic digestion processing. Such a material mass may include biological material including adipose tissue and enzyme for enzymatic digestion of the adipose tissue. The enzyme may be in an aqueous digestion medium added to the processing container to contact the adipose tissue in the internal fluid containment space. Such adipose tissue and aqueous digestion medium will initially typically be present in separate material phases at the start of enzymatic digestion processing before they have been substantially mixed together. It has been found that having the material mass, when in a quiescent state, not completely fill the internal fluid containment space is beneficial for quick and efficient enzymatic digestion of adipose tissue. In some preferred implementations, the material mass disposed in the internal fluid containment space during enzymatic digestion may have a quiescent volume corresponding with a quiescent partial fill volume of the internal fluid containment space in a range of from 30 percent to 75 percent, and preferably from 35 percent to 65 percent, of a maximum fluid fill volume capacity of the internal fluid containment space. A quiescent headspace volume in the internal fluid containment space above the quiescent partial fill volume may beneficially be in a range of from 25 percent to 70 percent of the maximum fluid fill volume capacity, and preferably from 35 percent to 65 percent of the maximum fluid fill volume capacity. In the reclined orientation, such quiescent partial fill volume may have a first vertical height in the internal fluid containment space and the quiescent headspace volume may have a second vertical height in the internal fluid containment space above the quiescent partial fill volume. In some preferred implementations, a ratio of such a second vertical height to the first vertical height may be in a range of from 1.4:1 to 0.3:1 in the reclined orientation. In some preferred implementations, a sum of the first vertical height and the second vertical height in the reclined orientation is in a range of from 40 millimeters to 140 millimeters. In some preferred implementations, the processing container has a maximum fluid fill volume capacity within the internal fluid containment space in a range of from 40 milliliters to 500 milliliters, and more preferably within a range of from 100 milliliters to 400 milliliters.

A method may include some tissue processing operations performed with the tissue processing unit in the upright orientation and other processing operations performed with the tissue processing unit in the reclined orientation. A method may include introducing a digestion medium into the internal fluid containment space prior to enzymatic digestion processing when the tissue processing unit is in the upright orientation. The digestion medium may be introduced into the internal fluid containment space through an unsealed inlet port that is later sealed for enzymatic digestion processing. Such digestion medium may be introduced as a prepared solution with enzyme to provide a desired concentration of enzyme for a process material mass in the internal fluid containment space for enzymatic digestion, or the digestion medium may be prepared in situ in the internal fluid containment space through addition of multiple components (e.g., enzyme concentrate and liquid buffer) introduced separately into the internal fluid containment space. A method may include introducing feed of biological material including adipose tissue into the internal fluid containment space when the tissue processing unit is in an upright orientation. The feed of biological material may be introduced through an unsealed inlet port that is later sealed for enzymatic digestion processing. Such feed of biological material may include lipoaspirate introduced directly into the internal fluid containment space during a lipoplasty procedure or may include biological material that has been subjected to some preliminary processing following a lipoplasty procedure during which lipoaspirate is initially extracted and before introduction into the internal fluid containment space. A method may include use of the tissue digestion system of the first-mentioned aspect of this disclosure and any operational features of such a tissue digestion system.

Numerous additional features and feature combinations of these and other aspects of this disclosure will become apparent to those skilled in the art upon consideration of the description and claims provided hereinbelow and the drawings.

DETAILED DESCRIPTION

Figure 1:
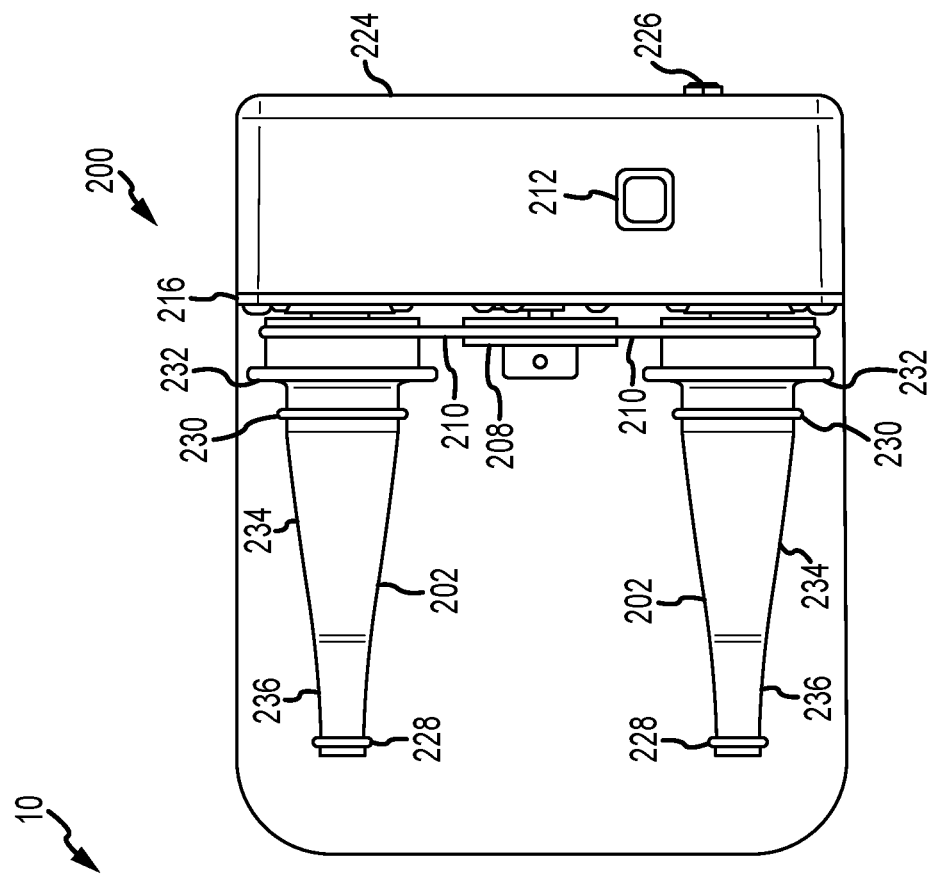
FIG. 1 illustrates an embodiment of a tissue digestion system for dissociation of and release of cellular components from adipose tissue, including a portable tissue processing unit shown in an upright orientation and a digestion drive unit to receive the tissue processing unit in a reclined orientation for rotational processing during enzymatic digestion processing of adipose tissue.
Figure 1:
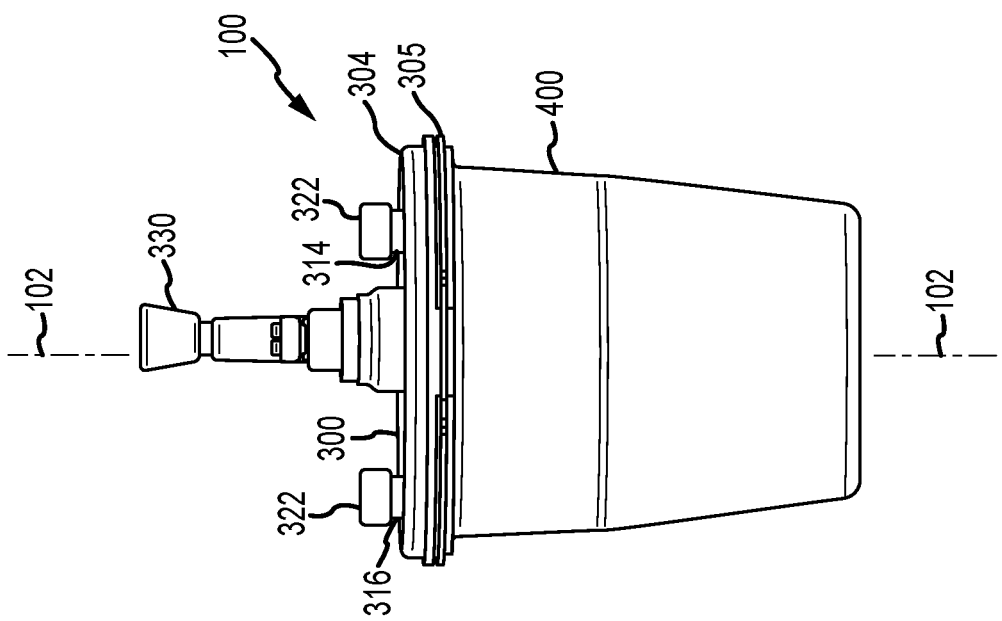

FIGS. 1-5 illustrate an example embodiment of a tissue digestion system 10 for dissociation of and release of cellular components from adipose tissue in biological material that may be processed using the tissue digestion system 10. The tissue digestion system 10 includes a portable tissue processing unit 100 in which biological material including adipose tissue is contained during enzymatic digestion processing. The tissue digestion system 10 also includes a digestion drive unit 200 configured to selectively receive the tissue processing unit 100 for enzymatic digestion processing that includes rotational processing of contents of the tissue processing unit 100. The tissue processing unit 100 is configured to be positioned in an upright orientation, as shown in FIG. 1, in which the tissue processing unit 100 is free-standing and conveniently oriented for access to input materials into or remove materials from a single-use processing container within the tissue processing unit 100. The tissue processing unit 100 is also configured to be positioned in a reclined orientation, as shown for example in FIGS. 2-5, for rotational processing by the digestion drive unit 200.

Various features of the digestion drive unit 200 and receipt and rotation of the tissue processing unit 100 in the reclined orientation by the digestion drive unit 200 will now be described with reference primarily to FIGS. 1-8.

The digestion drive unit 200 includes two longitudinally-extending rotational drive members 202 on which the tissue processing unit 100 rests and is supported for rotational processing when the tissue processing unit is received by the digestion drive unit 200 in the reclined orientation. Each rotational drive member 202 has a longitudinal axis 204 about which the rotational drive member 202 is rotated to drive rotation of the tissue processing unit 100. The digestion drive unit 200 includes an electric motor 206 having a rotational output shaft connected with a drive pulley 208. A rotational drive connection is made to the rotational drive members 202 through a drive belt 210 driven by the drive pulley 208. The drive belt 210 is engaged with a pulley track on the drive pulley 208 and pulley tracks on each of the rotational drive members 202. Operation of the electric motor 206 to drive rotation of the drive pulley 208 to drive rotation of the rotational drive members 202 is actuated by an on/off switch 212. In some implementations, the digestion drive unit 200 may be designed to operate at a set rotational speed for rotation of the tissue processing unit 100 when the digestion drive unit 200 is in the on mode, for ease of operation by a user. However, in some alternative implementations, the digestion drive unit 200 may include an adjustment mechanism through which a user may adjust the rotational speed of the motor 206 to adjust the rotational speed of the rotation of the tissue processing unit 100. For example, the digestion drive unit 200 may include a potentiometer or rheostat that is manipulable by the user through a user interface (e.g., knob or touch screen) to adjust the rotational speed through a range of available rotational speeds.

As illustrated, the drive belt 210 is engaged with both of the rotational drive members 202. In an alternative arrangement, such a drive belt 210 could be engaged with only one of the rotational drive members 202 while the other rotational drive member is not engaged with the drive belt and is free to rotate independent of the drive belt 210. In such an alternative arrangement, the engaged rotational drive member would be rotated by the drive belt 210 to impart the opposite-direction rotation of the tissue processing unit 100, while the other rotational drive member 202 that is not engaged with the drive belt 210 would be free to rotate to not interfere with the rotation of the tissue processing unit 100 as imparted by the engaged rotational drive member 202.

Each of the rotational drive members 202 is rotationally mounted adjacent a proximal end 214 of the rotational drive member 202 to be supported by a frame 216. Each rotational drive member 202 extends in a cantilevered manner from the frame 216 toward a free distal end 218 of the rotational drive member 202. As seen best in FIGS. 6 and 8, a proximal end portion of each rotational drive member 202 is disposed through a bearing unit 221 including a bearing housing 220 and two ball bearing units 222. The bearing unit 221 is mounted to the frame 216 to rotationally support the rotational drive member 202. The electric motor 206 and the bearing units 221 are conveniently disposed within a protective housing 224 through which the on/off switch 212 extends for convenient access by a user. An electrical plug receptacle 226 is located on a back side of the protective housing 224 to provide for making an electrical connection to the digestion drive unit 200 from an external power source to provide electrical power to the electric motor 206.

Figure 2:
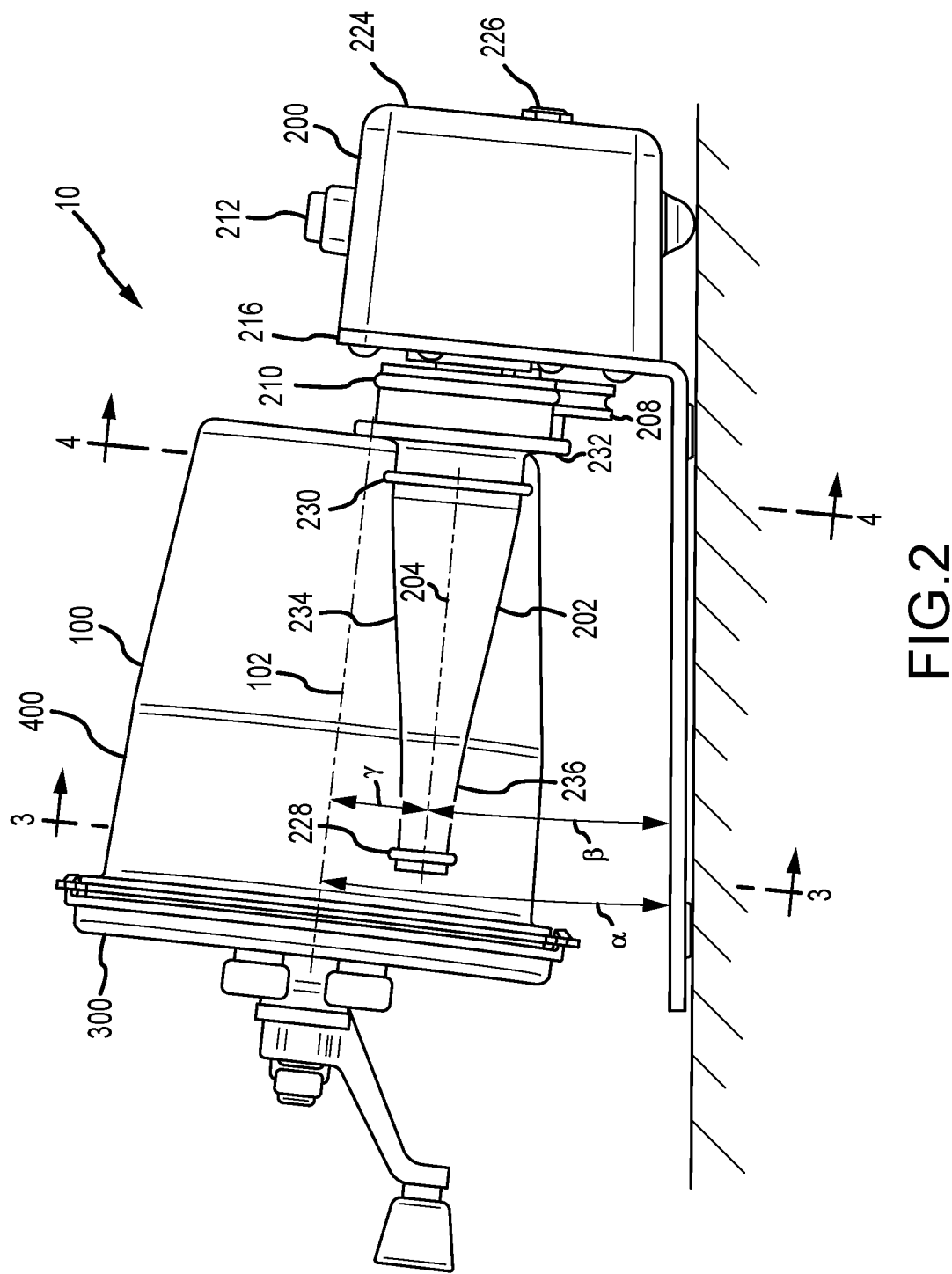
FIG. 2 illustrates a side view of the same embodiment of the tissue digestion system as shown in FIG. 1 with the tissue processing unit received by the digestion drive unit in a reclined orientation for rotational processing.
Figure 3:
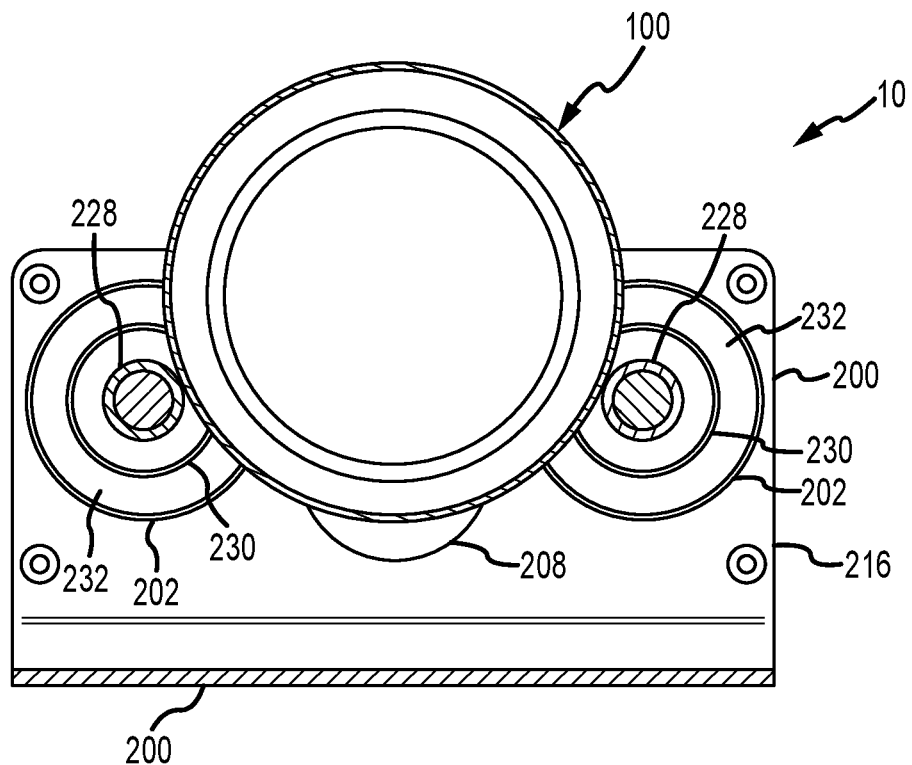
FIGS. 3 and 4 show sectional views of the same tissue digestion system as shown in FIG. 2 along section lines as indicated in FIG. 2.
Figure 4:
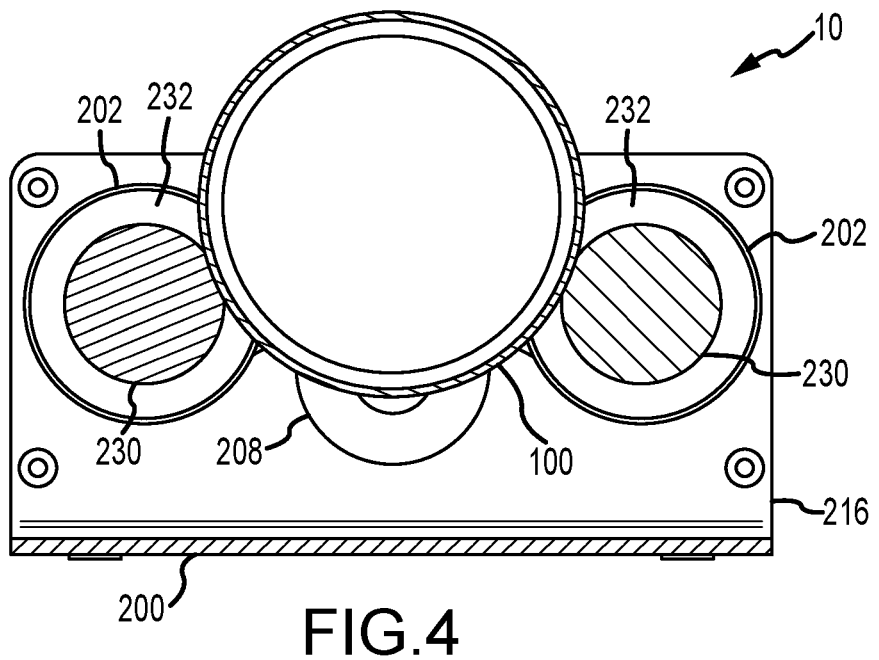

The rotational drive members 202 are positioned and have features designed to receive and retain the tissue processing unit 100 in a reclined orientation during rotational processing driven by the digestion drive unit 200 during enzymatic digestion processing. As seen best in FIGS. 2 and 6, the rotational drive members 202 are mounted in the digestion drive unit 200 with the longitudinal axes 204 inclined at an angle 13 relative to horizontal. Also as shown in FIG. 2, when the tissue processing unit 100 is received to be supported on the rotational drive members 202 in the reclined orientation, an axis of rotation 102 of the tissue processing unit 100 is at a slight angle γ relative to the longitudinal axes 204 of the rotational drive members 202. A result is that for the example tissue digestion system 10, in the reclined orientation as received by the digestion drive unit 200 for rotational processing, the axis of rotation 102 of the tissue processing unit 100 is inclined relative to horizontal at an angle of inclination of α that is the sum of the angles β and γ, and the axis of rotation 102 in this example is not parallel with the longitudinal axes 204. For example, if β is 5° and γ is 1°, then α, the angle of inclination of the axis of rotation 102 relative to horizontal, is 6°. The inclination of the longitudinal axes 204 of the rotational drive members 202 and the further inclination of the axis of rotation 102 relative to the longitudinal axes 204 help to retain the tissue processing unit 100 in position in a desired orientation during rotational processing of the tissue processing unit 100 by the digestion drive unit 200. To further assist retaining the tissue processing unit 100 in position in the desired orientation during rotational processing, each rotational drive member 202 includes a circumferential traction feature 228 disposed near the distal end 218 of each rotational drive member 202. In the example configuration of the digestion drive unit 200 shown in FIGS. 1-8, the traction feature 228 is illustrated as an elastomeric O-ring retained in a circumferential recess in a structural portion of the rotational drive member 202 made of a hard structural material, for example a metallic material (e.g., steel or stainless steel) or a hard engineering plastic. The traction feature 228 provides an enhanced frictional contact surface to help ensure that rotation of the tissue processing unit is driven at the desired rotational speed and to help prevent the tissue processing unit 100 from migrating in a distal direction along the rotational drive members 202 when the tissue processing unit 100 is being rotated by the rotational drive members 202. Each rotational drive member 202 also includes a circumferential support protrusion 230 disposed toward the proximal end 214 of the rotational driver member 202 relative to the traction feature 228. The support protrusions 230 are located to provide a support location on the rotational drive members 202 to support the tissue processing unit 100 during rotational processing. Each rotational drive member 202 also includes a distally-facing shoulder surface 232 against which a bottom of the tissue processing unit 100 is disposed to prevent migration of the tissue processing unit 100 in a proximal direction along the rotational drive members 202. Having the longitudinal axes 204 inclined by a small amount relative to horizontal also helps to prevent migration of the tissue processing unit in a distal direction along the rotational drive members 202 during rotational processing.

When the tissue processing unit 100 is received in the reclined orientation by the digestion drive unit 200, the tissue processing unit 100 is supported on its side by the traction feature 228 toward a top of the tissue processing unit 100 and by the support protrusions 230 toward the bottom of the tissue processing unit 100 and with the bottom of the tissue processing unit 100 abutting the shoulder surfaces 232. In the example illustrated in FIGS. 1-8, the support protrusions 230 are made of the same hard, structural material of the structural portion of the rotational drive members 202. This permits for some rotational slip between the support protrusions 230 and the tissue processing unit 100 while the elastomeric material of the traction features 228 provides good frictional contact between the rotational drive members 202 and the tissue processing unit 100 to positively drive the rotation of the tissue processing unit 100. In an alternative configuration, such support protrusions 230 could be of an elastomeric material similar to the traction features 228 to provide a second location for good frictional contact to drive rotation of the tissue processing unit 100. In the example illustrated in FIGS. 1-8, each rotational drive member 202 has a first longitudinal portion 234 along which the cross-section of the rotational drive member 202 tapers (reduces in size) along the longitudinal axis 204 in a direction from the proximal end 214 toward the distal end 218 of the rotational drive member 202. Each rotational drive member 202 also includes a second longitudinal portion 236, located distal of the first longitudinal portion 234, and the cross-sectional area of the rotational drive member 232 also tapers along the longitudinal axis 204 in a direction toward the distal end 218, but at a smaller rate of taper than the first longitudinal portion 234. The tapers along the first longitudinal portion 234 and the second longitudinal portion 236 generally correspond with corresponding external surface configurations of the tissue processing unit 100.

In the illustrated example of FIGS. 1-8, the rotational drive members 202 are in peripheral contact with the tissue processing unit 100, with the respective exterior surfaces of each rotational drive member 202 tangentially contacting an exterior surface of the side of the tissue processing unit 100. As may be appreciated, when the digestion drive unit 200 is operated to drive rotation of the rotational drive members 202, the drive belt 210 will drive rotation of both rotational drive members 202 in the same rotational direction (e.g., clockwise or counterclockwise) and rotation of the tissue processing unit 100 will be in an opposite rotational direction to the rotational direction of the rotational drive members 202. For example, if the rotational drive members 202 are rotated in a clockwise direction about the longitudinal axes 204 then the tissue processing unit 100 will rotate in a counterclockwise direction about the axis of rotation 102, and likewise if the rotation drive members 202 are rotated in a counterclockwise direction about the longitudinal axes 204 then the tissue processing unit 100 will rotate in a clockwise direction about the axis of rotation 102.

Various features of the tissue processing unit 100 will now be described with reference primarily to FIGS. 1 and 9-13.

Figure 5:
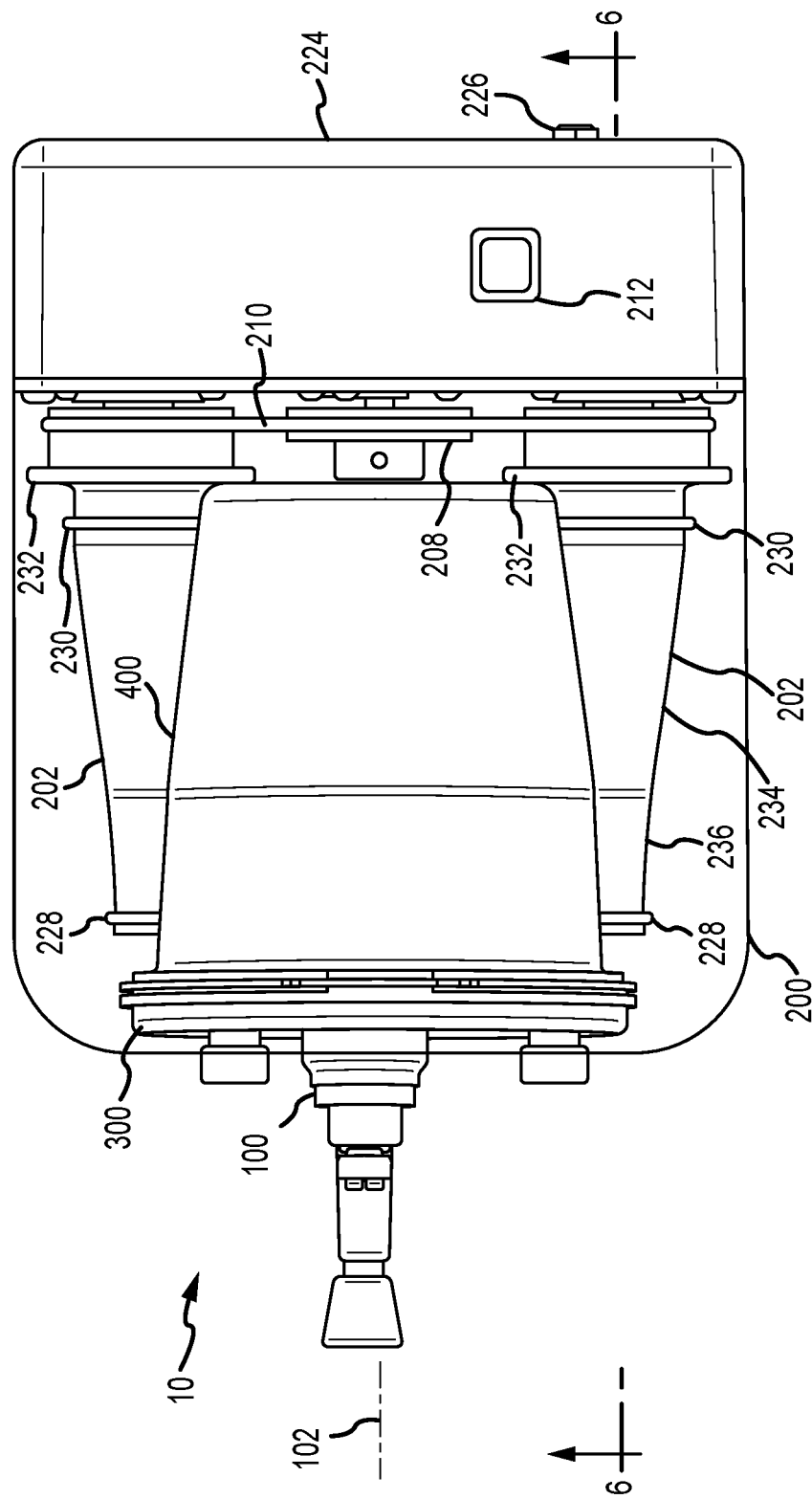
FIG. 5 illustrates a top view of the same embodiment of the tissue digestion system as shown in FIGS. 1-4 with the tissue processing unit received by the digestion drive unit in a reclined orientation for rotational processing.
Figure 6:
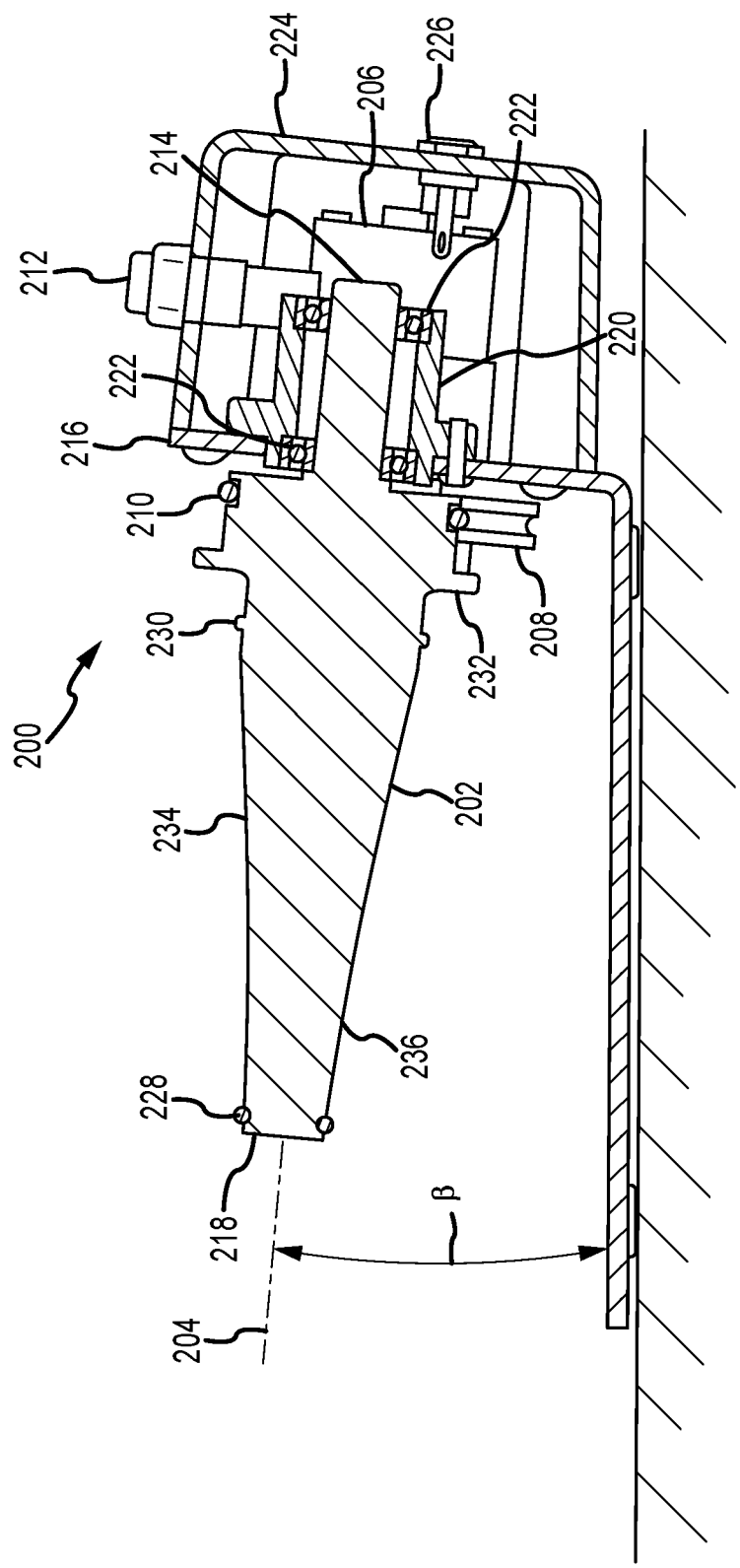
FIG. 6 shows a sectional view of the digestion drive unit of the embodiment of the tissue processing system illustrated in FIGS. 1-5 along a section line as indicated in FIG. 5.
Figure 7:
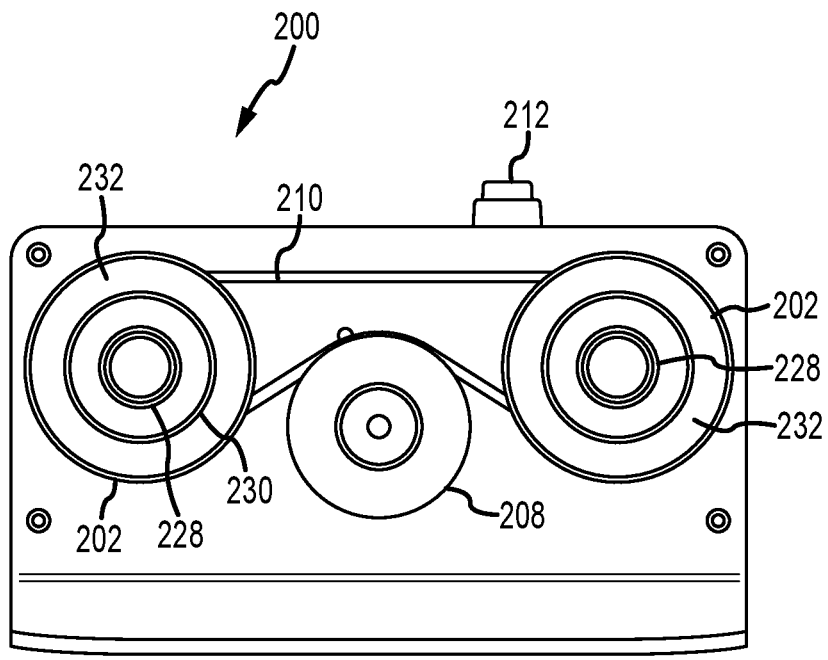
FIG. 7 illustrates a front view of the digestion drive unit of the embodiment of the tissue processing system illustrated in FIGS. 1-5.
Figure 8:
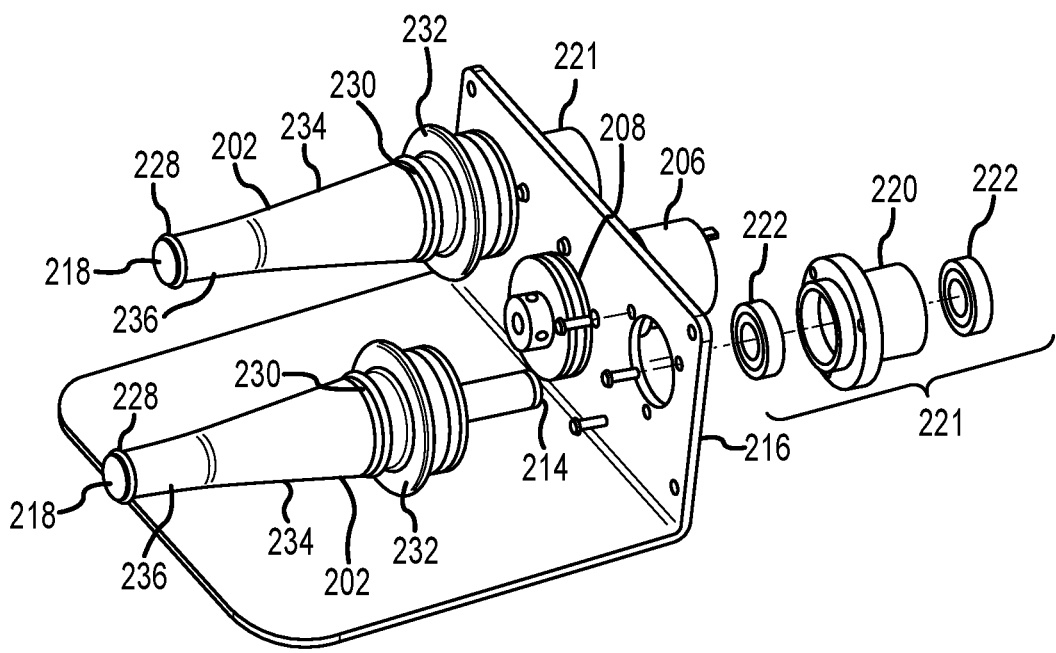
FIG. 8 illustrates a partially-exploded perspective view of features of the digestion drive unit of the embodiment of the tissue processing system illustrated in FIGS. 1-5.
Figure 9:
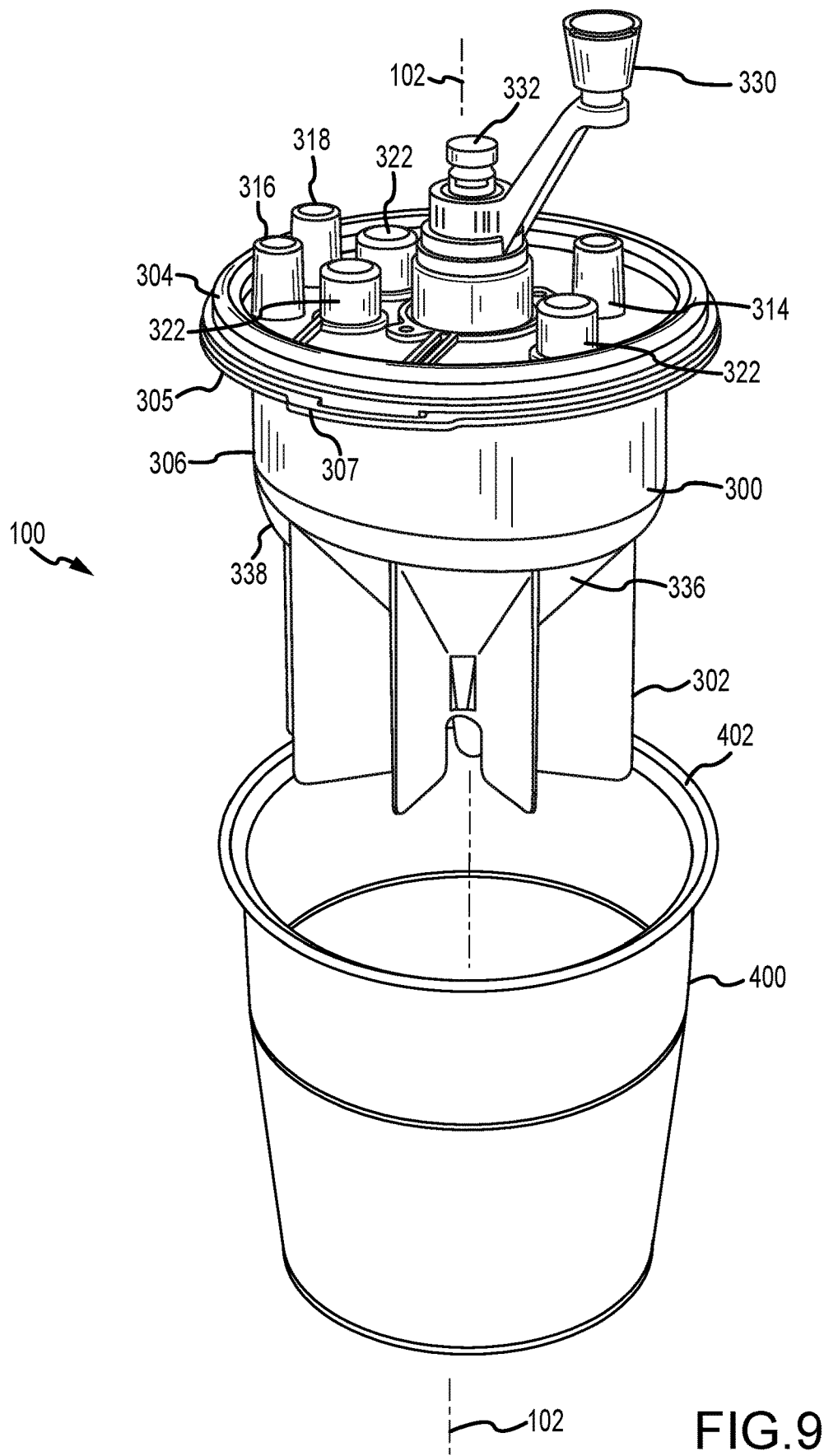
FIG. 9 illustrates an exploded perspective view of a portable container apparatus configuration and protective processing sleeve configuration for the tissue processing unit of the embodiment of the tissue processing system illustrated in FIGS. 1-5.
Figure 10:
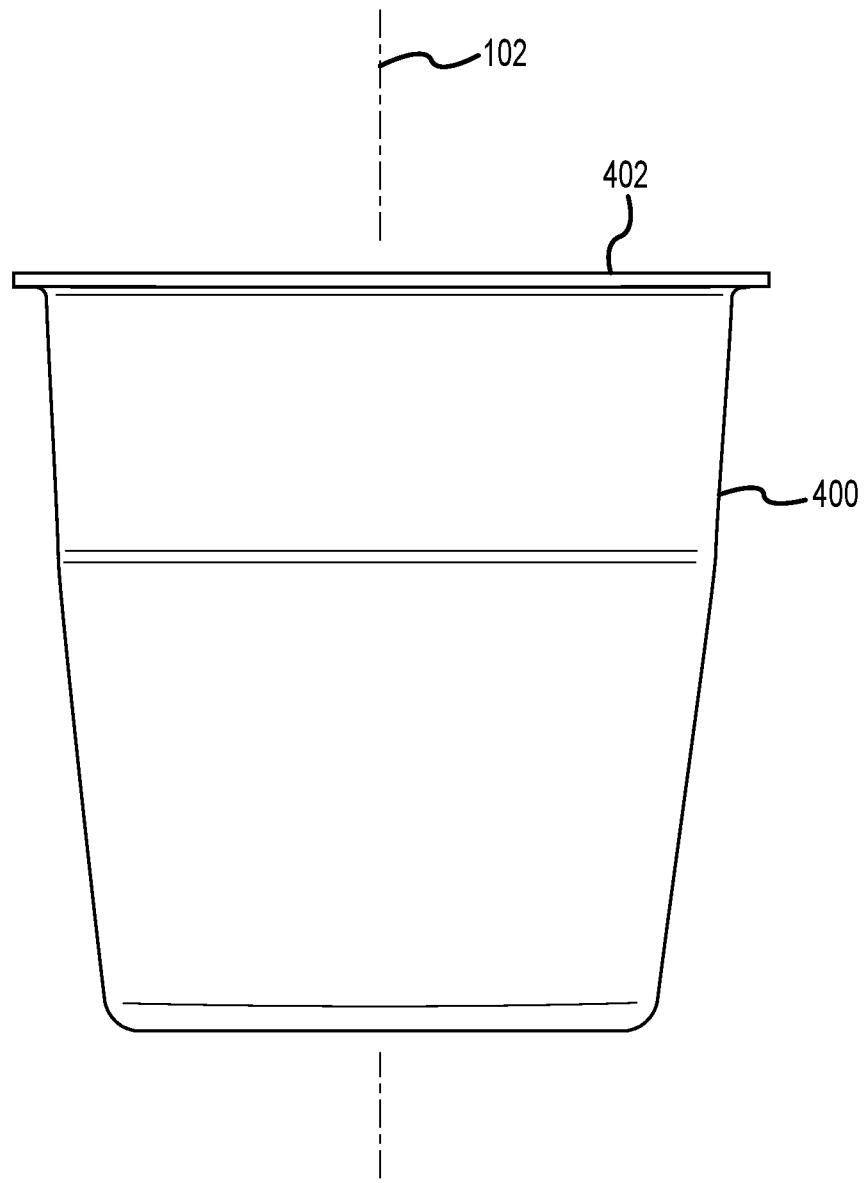
FIG. 10 illustrates a side view of the protective processing sleeve illustrated in FIG. 9.

As shown in FIGS. 1 and 9, the tissue processing unit 100 includes a portable container apparatus 300 and a protective processing sleeve 400. As illustrated in FIG. 9, most of the container apparatus 300, including the bottom of the container apparatus 300, is inserted into and removably received within the processing sleeve 400 through an open top 402 of the processing sleeve 400. The processing sleeve 400 is in the form of an open-top container sized to receive the container apparatus 300 except for a top portion of the container apparatus 300 including a lid 304 of the container apparatus 300 that remains outside of the processing sleeve 400 and projects above the top 402 of the processing sleeve 400 when the tissue processing unit 100 is in the upright orientation. A flanged lip portion 305 of the container apparatus 300 projects laterally to a side of the top edge of the processing sleeve 400. With this configuration, as seen in FIGS. 2 and 5, when the tissue processing unit 100 is received by the tissue digestion unit 200 in the reclined orientation, the tissue processing unit 100 is in contact with digestion drive unit 200 only at outside surfaces of the processing sleeve 400. The digestion drive unit 200 is not in contact with the container apparatus 300. A top portion of the container apparatus 300 projecting from the open end of the processing sleeve 400 projects in a cantilevered manner distal of the distal ends 218 of the rotation drive members 202. As may be appreciated, processing equipment such as the digestion drive unit 200 may be difficult to maintain in a completely sterile state, and limiting contact between the tissue processing unit 100 and the digestion drive unit 200 to outside surfaces of the processing sleeve 400 protects the container apparatus 300 from contact with potentially non-sterile surfaces of the digestion drive unit 200.

Figure 11:
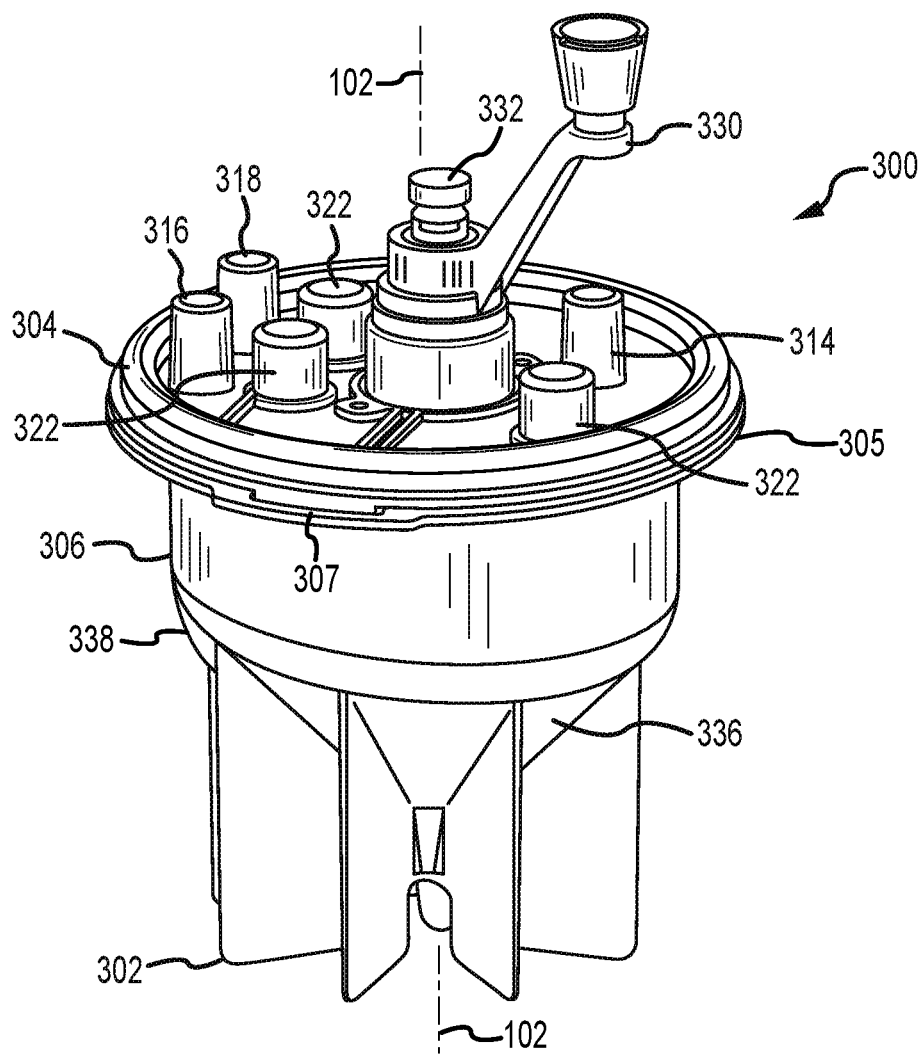
FIG. 11 illustrates a perspective view of the portable container apparatus illustrated in FIG. 9.
Figure 12:
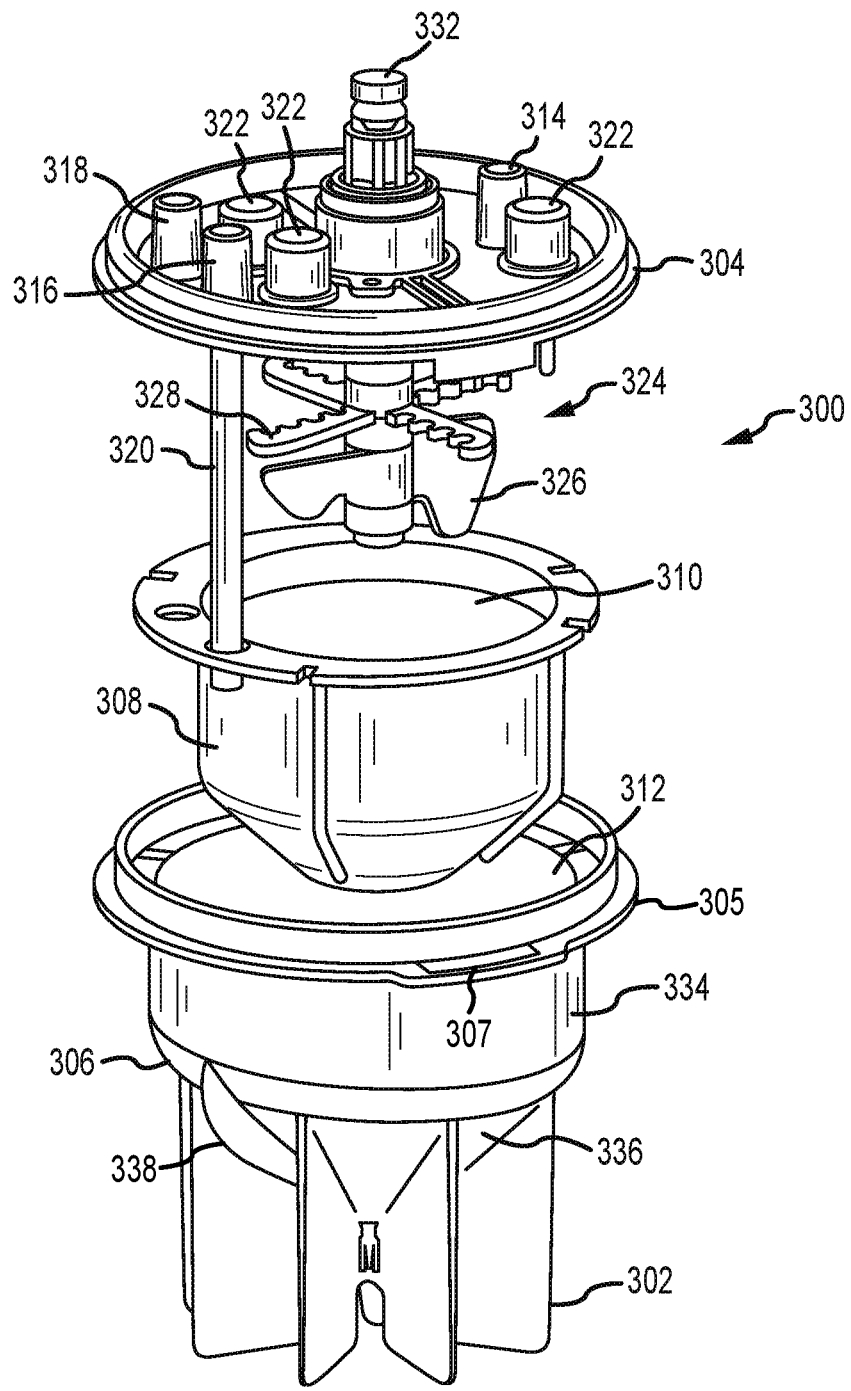
FIG. 12 illustrates an exploded perspective view showing features of the portable container apparatus illustrated in FIGS. 9 and 11.

After all processing of contents within the container apparatus 300 is completed, the container apparatus 300 may be removed from the processing sleeve 400 still in a sterile condition. As shown in FIGS. 9, 11 and 12, the lip portion 305 of the container apparatus 300 includes handle projections 307 on opposing sides of the lip portion 305 that provide convenient surfaces for a user wearing sterile gloves to grip the top portion of the container apparatus 300 and lift it out of the processing sleeve 400 without touching the processing sleeve 400.

Various features of the container apparatus 300 will now be described with reference primarily to FIGS. 9 and 11-13.

The container apparatus 300 is shown positioned in FIGS. 9 and 11-13 as it would be in the upright orientation, with the axis of rotation 102 extending vertically through the container apparatus 300 (inclined by 90° relative to horizontal) in the illustrated example. The container apparatus 300 has base supports 302 (not shown in FIG. 13) on which the container apparatus 300 may be supported in a free-standing, upright orientation when not received in the processing sleeve 400. The container apparatus 300 includes the lid 304 and a bowl-like shell 306, which together make up a container providing an internal fluid containment space within the container.

In the illustrated example, the flanged lip portion 305 is provided on a top portion of the shell 306. A filter 308 divides the internal fluid containment space into a tissue retention portion 310 inside the filter 308 between the filter 308 and the lid 304 and a filtrate portion 312 disposed on the other side of the filter 308 between the filter 308 and the shell 306. An inlet port 314 provides access to the tissue retention portion 310 of the internal fluid containment space, for example to introduce adipose tissue into the tissue retention portion 310 for processing. A suction port 316 and an additional port 318 (e.g., second suction port or vent port) provide access to the filtrate portion 312, for example to suction fluids from the filtrate portion 312. The suction port 316 is connected with a suction conduit 320 extending from the suction port 316 to within a tapered portion of the internal fluid containment space of the container apparatus 300. Caps 322 attached to the lid 304 may be used to cover and seal the suction port 316, additional port 318 and inlet port 314 as needed. The container apparatus 300 includes a rotatable assembly 324 including a mixing impeller 326 with pitched blades, a tissue collector 328 and mixing paddles 340 mounted on a rotatable shaft. The rotatable shaft is rotatable by a hand-manipulable handle 330 (shown in FIGS. 1 and 11). A lumen extends through the rotatable shaft to provide access from outside of the container apparatus 300 into the internal fluid containment space of the container apparatus. The container apparatus 300 is shown fitted with a cap 332 that may be removed to permit access to the lumen through the rotatable shaft. The tissue collector 328 of the rotatable assembly 324 may help to collect stringy tissue components that may be present to inhibit plugging of the filter 308 by such stringy tissue components. The container apparatus 300 has a generally circular container cross-section at all elevations through the internal fluid containment space in the upright orientation, which is beneficial for rotational processing in a reclined orientation during an enzymatic digestion operation. As seen in FIGS. 1, 9 and 11-13, in the illustrated example of the tissue processing apparatus 100, the axis of rotation 102 is parallel to but not coincident with the longitudinal axis of the rotatable shaft of the container apparatus 300. The rotatable shaft is positioned slightly to a side of a central axis of the tissue processing unit 100, and of the container apparatus 300, to provide clearance for the rotating features of the rotatable assembly relative the suction conduit 320.

The shell 306, and the internal fluid containment space within the shell 306 and the lid 304, includes a first portion 334 and a second portion 336. The first portion 334 includes a portion of the internal fluid containment space that has a substantially circular cross-section that either does not taper (e.g., is cylindrical) or that tapers only minimally. In that regard, the internal wall surface of the first portion 334 may in the upright orientation be inclined relative to horizontal at an angle of from 70° to 90°. The second portion 336 includes a portion of the internal fluid containment space that tapers at a significant rate in a direction toward the bottom of the apparatus 300. The internal wall surface of the second portion 336 may in the upright orientation preferably be inclined relative to horizontal at an angle in a range having a lower limit of 30°, 35°, 40°, 42° or 45° and an upper limit of 60°, 55°, 50°, 48 or 45°, with about 45° being preferred for some implementations. The second portion 336 may taper downward toward a pellet well 342 (shown in FIG. 13) configured to conveniently collect pellet phase material including stromal vascular fraction cells when the container apparatus 300 is centrifuged following completion of enzymatic digestion processing. The pellet well 342 may include a third portion of the internal fluid containment space that in the upright orientation does not taper in a downward direction or that tapers in a downward direction with an internal wall surface that may preferably be inclined relative to horizontal at an angle in a range having a lower limit of 70°, 75°, 80 or 85° and an upper limit of 90°. The first portion 334 may include a cylindrical shape or a frustoconical shape. The second portion 336 may include a frustoconical shape. The third portion within the pellet well 342 may include a cylindrical shape or a frustoconical shape.

A lower portion of the suction conduit 320 is retained in an appropriate configuration through the second portion 336 of the internal fluid containment space in a corresponding trough feature 338. For example, the suction conduit 320 may be a flexible tube that is deflected and guided by the trough feature 338 to a desired location in the second portion 336 where it is desired to suction fluid from the filtrate portion 312 of the internal fluid containment space for removal through the suction portion 318. The container configuration of the container apparatus may for example be or have features as described in U.S. Pat. No. 9,296,984 or U.S. Patent Application Publication No. 2016/0208211, each of which is incorporated herein by reference.

During tissue processing, feed of biological material including adipose tissue may be introduced into the tissue retention portion 310 of the internal fluid containment space through the inlet port 314. Such feed of biological material for processing in the container apparatus 300 may conveniently include lipoaspirate introduced directly into the container apparatus 300 during a lipoplasty operation (e.g., liposuction), or may include biological material originally sourced from lipoaspirate that has been subjected to some preliminary clean-up or other preliminary processing before introduction into the tissue retention portion 310 of the internal fluid containment space of the container apparatus 300.

Reference is now made primarily to FIGS. 13-17 to describe various features of the portable container apparatus 300 in connection with enzymatic digestion processing. FIGS. 13-17 each illustrates the container portion of the container apparatus 300 with the walls of the container formed by the lid 304 and the shell 306 shown in sectional view and showing internal features of the container apparatus 300. For convenience of illustration, the base supports 302 are not shown in FIGS. 13-17. FIGS. 13-17 show the geometry within the container apparatus 300 of the internal fluid containment space, including for the tissue retention portion 310 inside of the filter 308 and the filtrate portion 312 outside of the filter 308. In the example design shown in FIGS. 13-17, the container apparatus 300 is designed to permit centrifugation of the container apparatus 300 following enzymatic digestion processing to form a pellet containing stromal vascular fraction in the pellet well 342 disposed in a bottom portion of the internal fluid containment space. In all of the illustrations of FIGS. 13-17, the container apparatus is shown with the fluid caps 322 in place on the corresponding ports to seal the ports to fluid communication as may be the case during normal processing operations to process biological material within the internal fluid containment space of the container apparatus 300.

Figure 13:
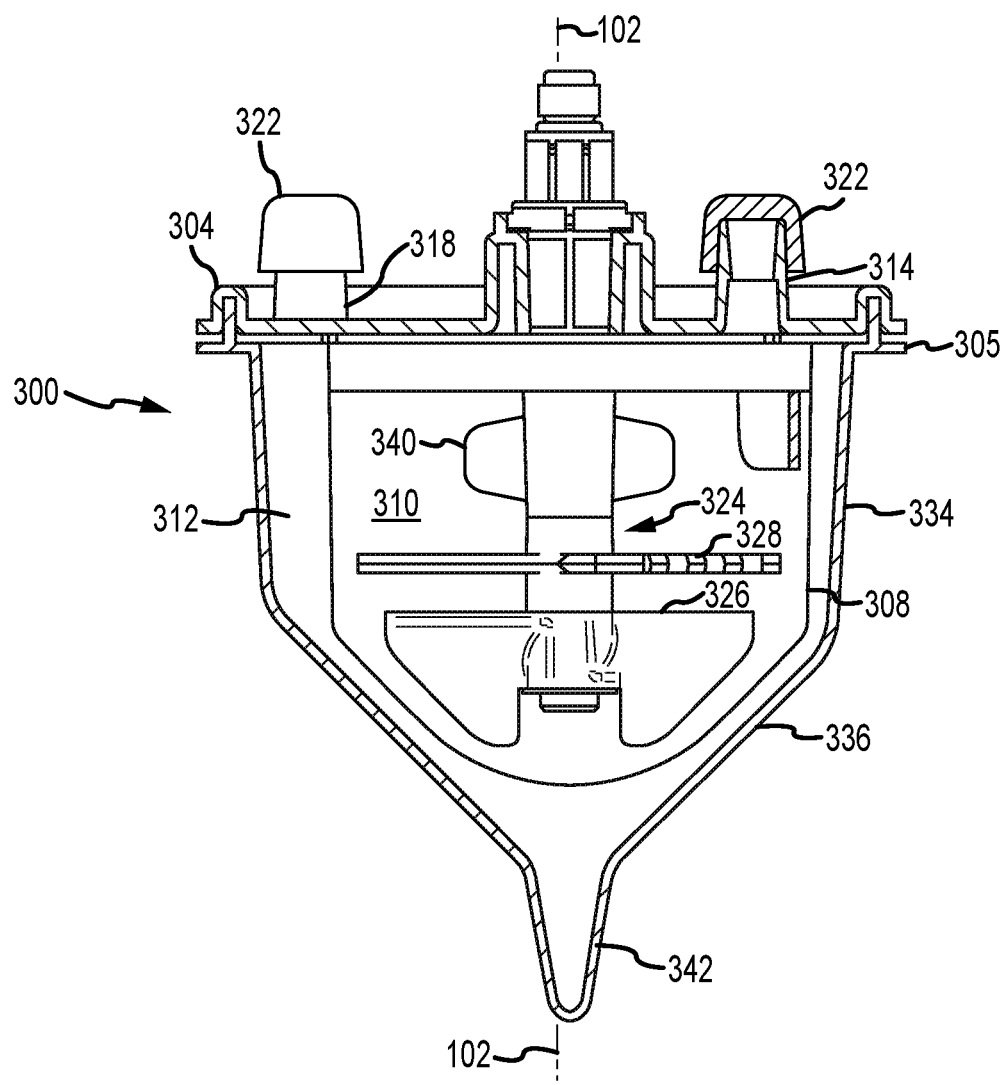
FIG. 13 illustrates a sectional view of a container portion of the portable container apparatus illustrated in FIGS. 9 and 11 shown in an upright orientation and showing internal equipment configurations in the internal fluid containment space in the container.
Figure 14:
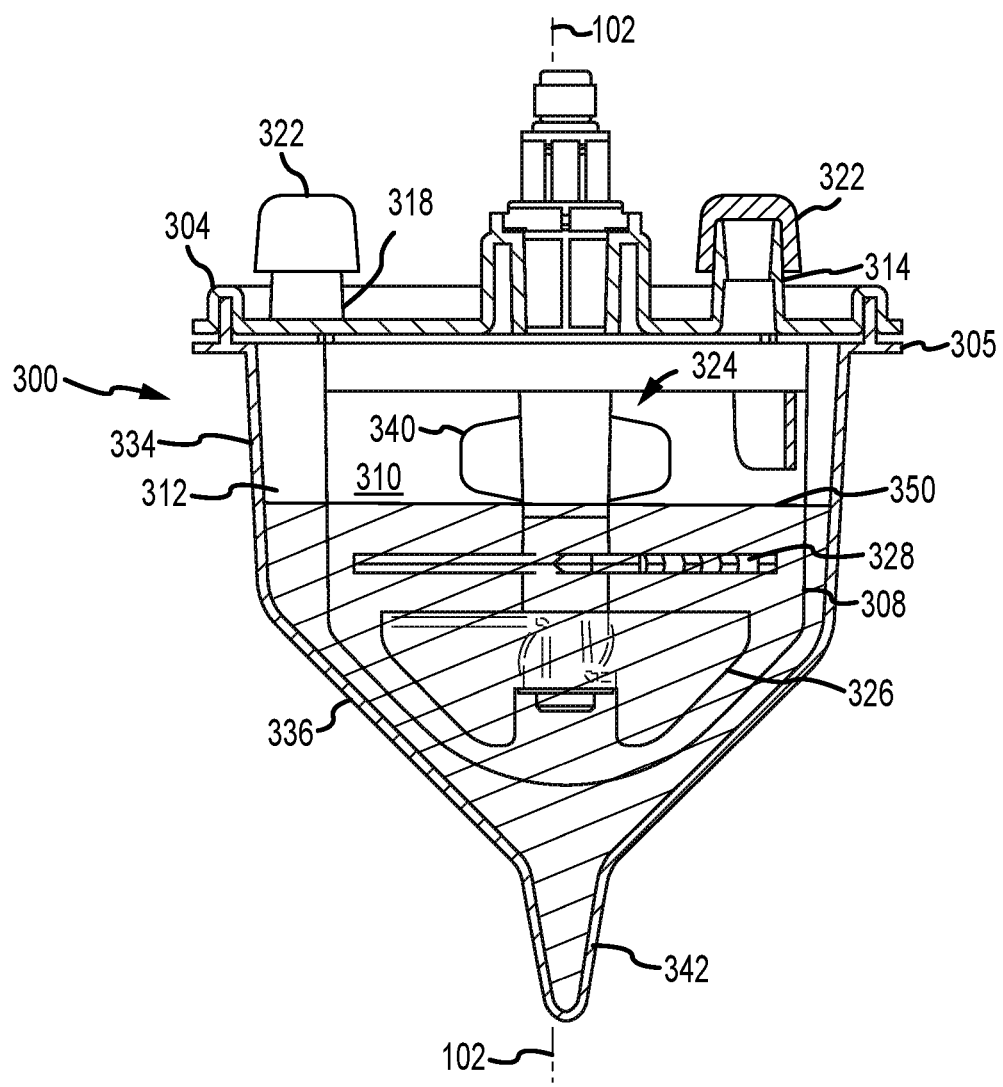
FIGS. 14-17 illustrate the same container portion as illustrated in FIG. 13 showing disposition of an example processing material mass disposed in the internal fluid containment space in the container and with the container in an example upright orientation in FIG. 14 and in three different example reclined orientations in FIGS. 15-17.
Figure 15:
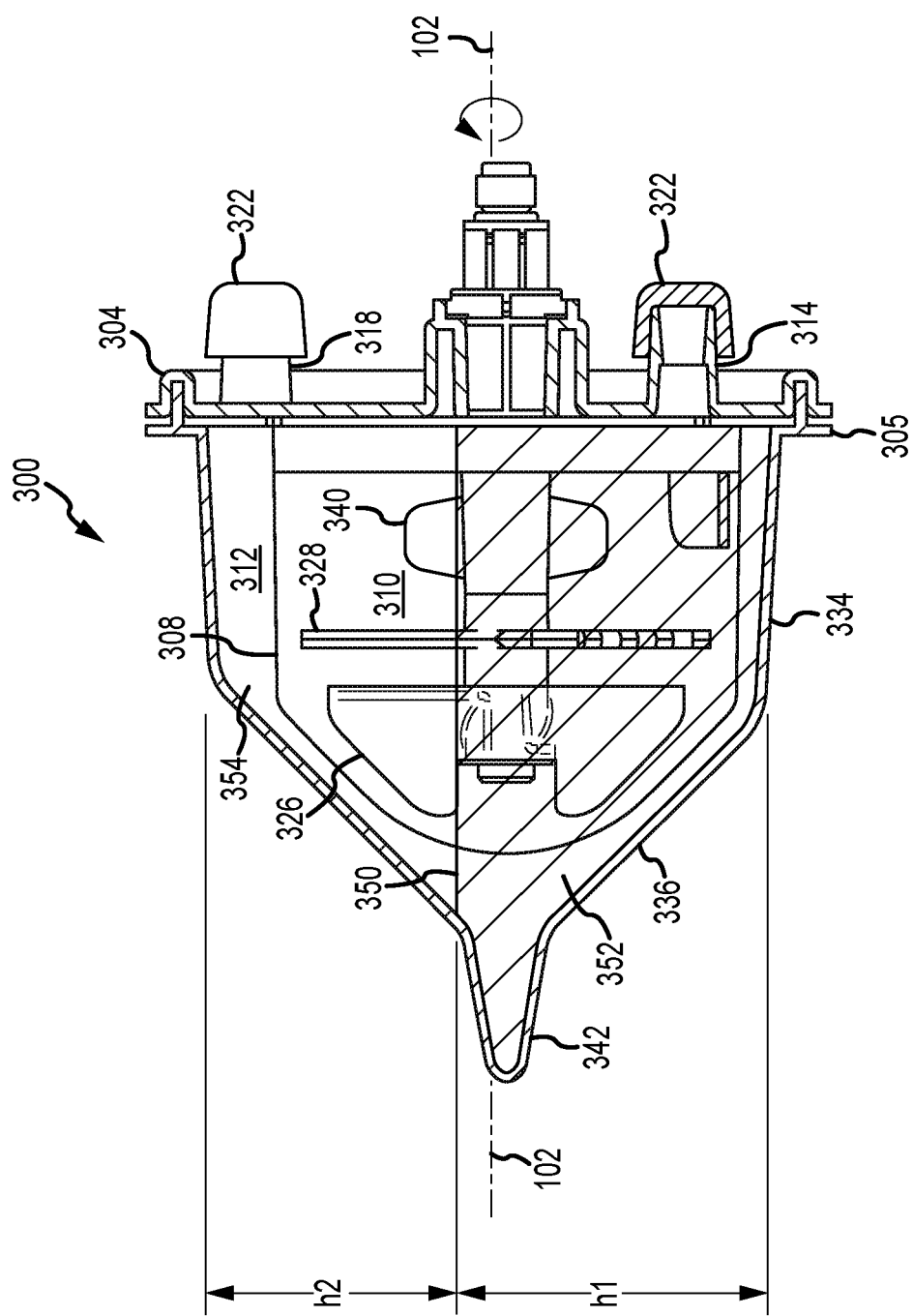
Figure 16:
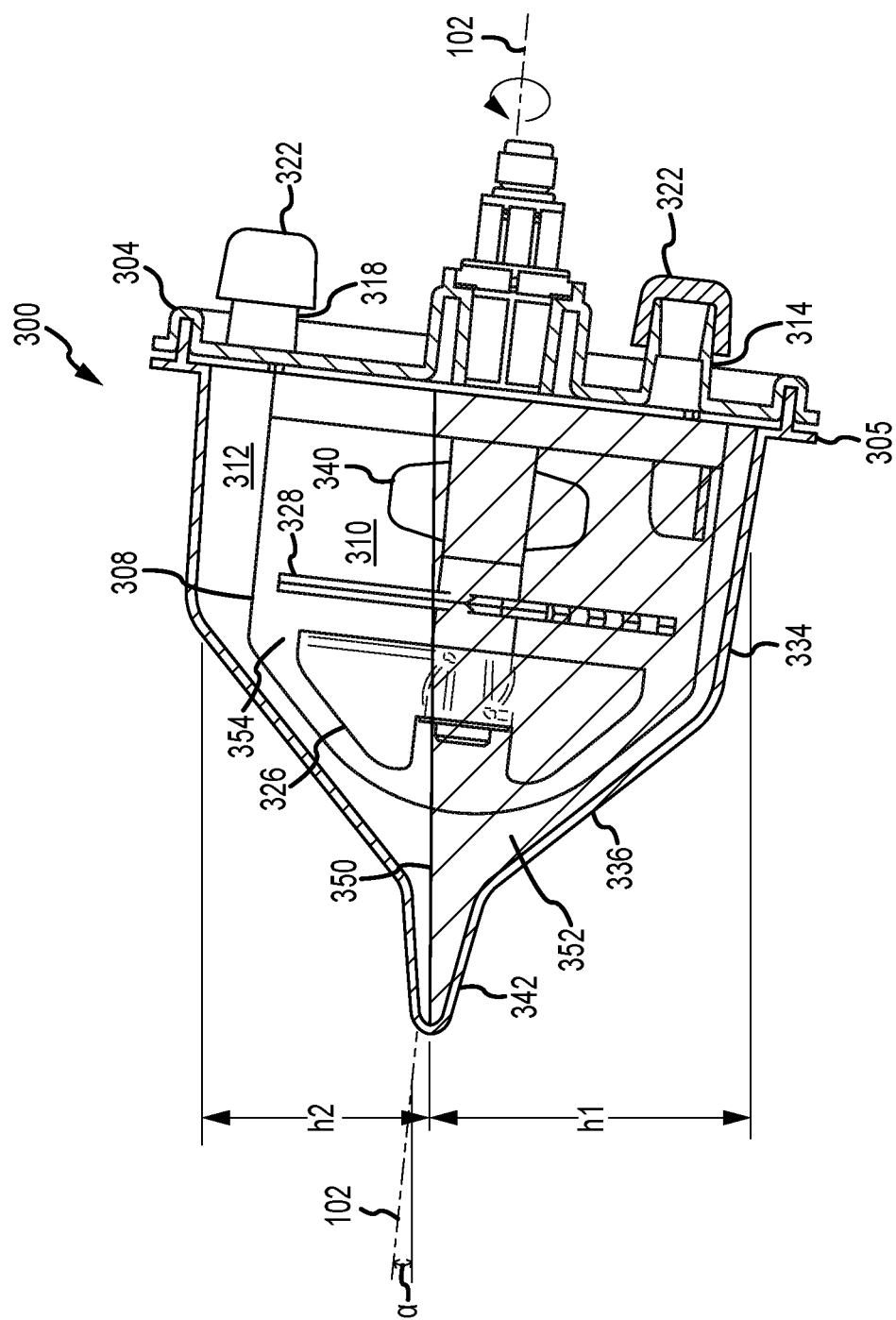
Figure 17:
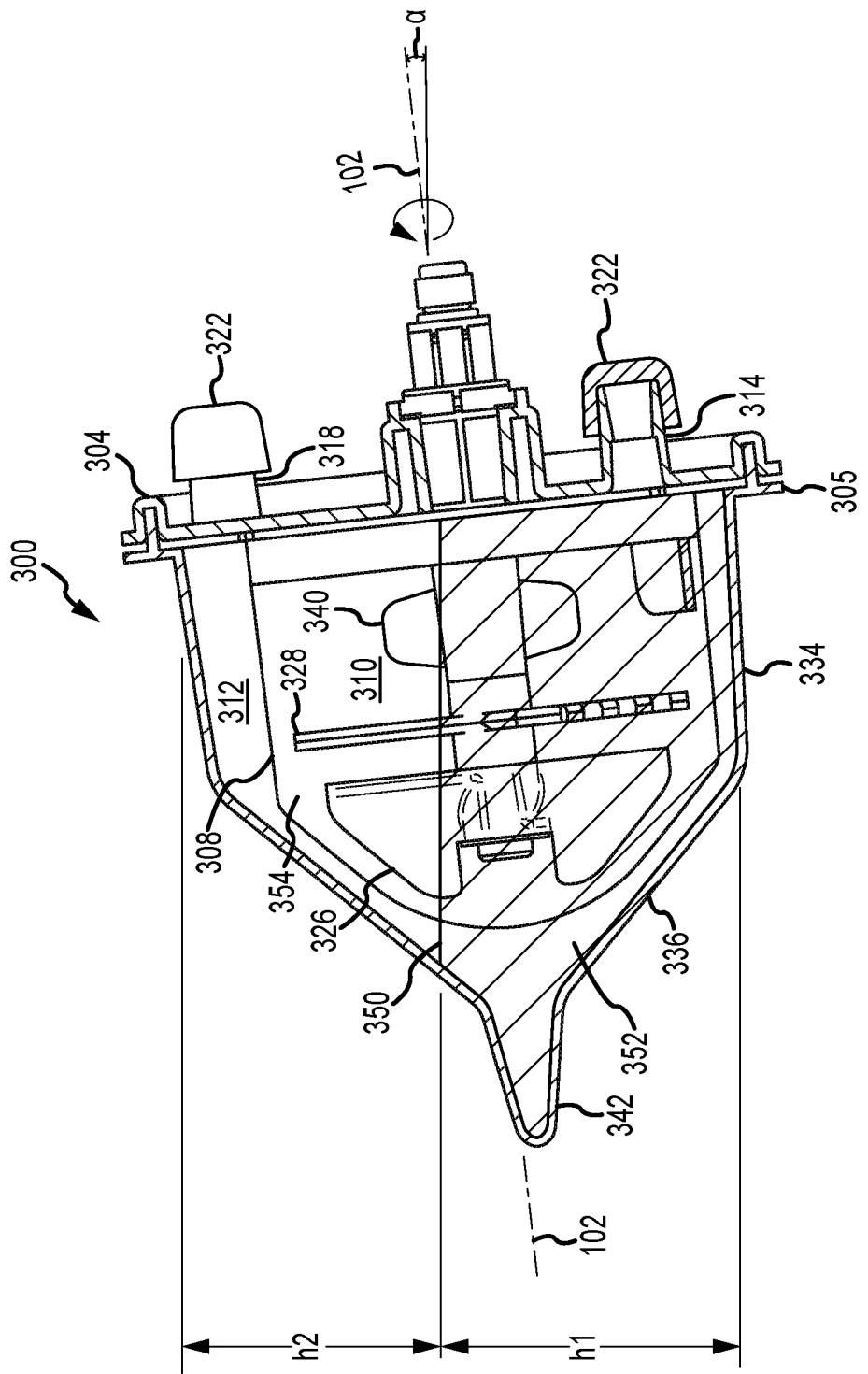

FIGS. 13 and 14 each shows the container apparatus 300 as positioned in an upright orientation with the axis of rotation 102 extending vertically in the illustrated example (inclined at an inclination angle of 90° relative to horizontal). FIG. 13 is shown with the internal fluid containment space empty of materials to be processed and FIG. 14 shows an example process material mass 350 in a quiescent state (not in an agitated state) disposed in the internal fluid containment space for processing. The process material mass 350 includes material to be processed within the internal containment space of the container apparatus 300. Such a process material mass 350 may include biological material containing adipose tissue and enzyme for digestion processing and any desired process liquids. As may be appreciated, the process material mass 350 may include multiple identifiable material phases, for example a distinct material phase of biological material initially made up primarily of adipose tissue and a separate apparatus liquid phase of digestion medium. FIGS. 15-17 show the container apparatus 300 in different example reclined orientations for rotational processing during enzymatic digestion processing, and with the same process material mass 350 shown in a quiescent state but redistributed within the internal fluid containment space with repositioning of the container apparatus 300 from the upright orientation as shown in FIG. 14 to the example reclined orientations shown in FIGS. 15-17. For illustration purposes, the process material mass 350 is shown filling about 60 percent of the maximum fluid fill volume capacity of the internal fluid containment space within the container apparatus 300. Each of FIGS. 13-17 shows that the rotatable assembly 324 includes the mixing paddles 340 in addition to the impeller blades 326 and tissue collector 328. In FIG. 12, the mixing paddles 340 are not seen because in that view they are concealed by the lid 304. As may be appreciated, in the illustrations of FIGS. 14-17 the adipose tissue in the process material mass 350 prior to enzymatic digestion may be disposed essentially entirely within the tissue retention portion 310 of the internal fluid containment space, and digestion medium may be disposed mostly in the filtrate portion 312 of the internal fluid containment space, although some digestion medium may also be present mixed with or disposed above the adipose tissue in the tissue retention portion 310. It is common that digestion medium, typically in the form of an aqueous liquid, added to or prepared in-situ within the internal containment space forms a separate, identifiable material phase distinct from the biological material. An important aspect of processing with the tissue digestion processing system and methods disclosed herein is enhanced introduction of digestion medium into interior portions of the biological material to promote more uniform contact of biological material with the enzyme and accordingly a more uniform and complete dissociation of adipose tissue during enzymatic digestion processing to enhance release of cellular components from the adipose tissue.

FIG. 15 illustrates the container apparatus 300 repositioned in a reclined orientation in which the axis of rotation 102 extends horizontally (inclined at an angle of inclination of 0° relative to horizontal) and showing the process material mass 350 in a quiescent state redistributed within the internal fluid containment space. In the reclined orientation, the quiescent process material mass 350 occupies a quiescent partial fill volume 352 of the internal fluid containment space and with a quiescent headspace volume 354 in the internal fluid containment space located above the quiescent partial fill volume 352 of the process material mass 350. When the tissue processing unit 100 is rotated about the axis of rotation 102 during enzymatic digestion processing, the container apparatus 300 also rotates about the axis of rotation 102. When the container apparatus 300 rotates about the axis of rotation 102, the rotatable assembly 324 rotates as a unit with the container. Permitting the rotatable assembly 324 to be rotated relative to the container of the container apparatus 300 through use of the handle 330, while having the rotatable assembly 324 rotate with the container (and not relative to the container) during the rotational processing is accomplished in the illustrated example of the container apparatus 300 through an O-ring that seals around the rotatable shaft in the top assembly of the container apparatus where the rotatable shaft is supported by the lid 304. It has been found that such a sealing O-ring that is pressed against the rotatable shaft with sufficient force to seal around the rotatable shaft while still permitting hand rotation of the rotatable shaft relative to the sealing O-ring to drive rotation of the rotatable assembly 324 provides sufficient frictional contact between the sealing O-ring and the rotatable shaft to prevent rotation of the rotational shaft relative to the sealing O-ring when the container apparatus 300 is subjected to the rotational processing by the digestion drive unit, so that the container and the rotational assembly 324 rotate as a unit and not relative to each other during the rotational processing. In one enhancement, the container apparatus 300 may include a locking mechanism, such as a slidable pin or latch, to selectively lock and unlock the rotatable shaft in position relative to the container to not permit or permit use of the handle 330 to rotate the rotatable shaft and the rotatable assembly relative to the container.

As the rotatable assembly 324 rotates as a unit with the container apparatus 300, each mixing blade of the mixing paddles 340 and the mixing impellers 326 have a portion that cycles between the quiescent partial fill volume 352 and the quiescent headspace volume 354. This cycling of mixing blades between the quiescent partial fill volume 352 and the quiescent headspace volume 354 beneficially promotes mixing of aqueous digestion medium into interior portions of the biological material contained in the process material mass 350. As each mixing blade moves from the quiescent headspace volume 354 into and through the process material mass 350, digestion medium tends to be pulled into and through the biological material containing the adipose tissue to be dissociated during the enzymatic digestion. Likewise as each such mixing blade moves from the process material mass 350 into the quiescent headspace volume 354, biological material tends to be pulled through and mixed with digestion medium. For enhanced benefit, the rotational speed of rotation about the axis of rotation is maintained at a relatively slow speed (e.g., from 5 to 40 revolutions per minute) in which the process material mass 350 does not become frothy and remains mostly contained within the quiescent partial fill volume 352, although some of the process material mass 350 may splash or be temporarily pulled out of the quiescent partial fill volume due to rotation of the tissue processing unit 100 and action of the mixing blades. The relatively slow rotational speed results in a folding-like effect where digestion medium and biological material are beneficially folded into and through one another, enhancing access of enzyme to interior portions of the biological material to more uniformly contact all portions of the biological material and consequently to more uniformly and more completely dissociate adipose tissue throughout the process material mass 350. In contrast, if the rotational speed of rotation about the axis of rotation 102 becomes too large, significant quantities of air may be pulled into and dispersed throughout the process material mass 350, which may develop into a frothy mixture with entrained gas domains which inhibit contact between enzyme and biological material and accordingly inhibit effective, uniform enzymatic digestion of adipose tissue.

FIG. 15 also illustrates relative vertical heights of the quiescent partial fill volume 352 ($h_1$) of the process material mass 350 and of the quiescent headspace 354 volume ($h_2$) disposed above the quiescent partial fill volume 352. As shown in FIG. 15, each mixing blade of the mixing paddles 340 and the mixing impeller 326 projects entirely into the quiescent partial fill volume 352 at times during a rotational cycle and at other times a significant distal portion of each such mixing blade projects into the quiescent headspace volume 354 above the quiescent partial fill volume 352.

FIGS. 16 and 17 each illustrate the container apparatus 300 repositioned from the upright orientation into example reclined orientations in which the axis of rotation 102 in each case is inclined relative to horizontal at the same example angle of inclination, $\alpha$, although inclining in opposite directions relative to horizontal. The example reclined orientation shown in FIG. 17 corresponds to a reclined orientation for the tissue processing unit 100 as illustrated in FIG. 2 in which the bottom of the container apparatus 300 is tipped up relative to the top of the container apparatus 300. Other than the different direction of the angle of inclination relative to horizontal in the examples of FIGS. 16 and 17, features and operation of the container apparatus 300 for rotational processing during enzymatic digestion processing are the same as described above with respect to FIG. 15, in which portions of the mixing blades of the mixing impeller 326 and mixing paddles 340 cycle between the quiescent partial fill volume 352 and the quiescent headspace volume 354.

FIGS. 16 and 17 each illustrates the relative vertical heights of the quiescent partial fill volume 352 ($h_1$) of the process material mass 350 and of the quiescent headspace volume 354 ($h_2$) in those example reclined orientations. The first vertical height $h_1$ represents a vertical separation between bottommost and topmost points in the quiescent partial fill volume 352 and likewise the second vertical height $h_2$ represents the vertical separation between bottommost and topmost points in the quiescent headspace volume 354. As may be appreciated, the values for $h_1$ and $h_2$, and the ratio between them, may change depending on the geometry of the internal fluid containment space within the container apparatus 300 and the angle the inclination of the axis of rotation 102 relative to horizontal in the reclined orientation. For example, in the examples of FIGS. 16 and 17, each of $h_1$ and $h_2$ is slightly larger than in FIG. 15 due to the angle of inclination in FIGS. 16 and 17 (angle $\alpha$ in opposing directions of inclination) relative to FIG. 16 (0° angle of inclination).

An example implementation of a method for processing biological material including adipose tissue to dissociate and release cellular components from the adipose tissue is now described with reference primarily to FIG. 18. The example method implementation illustrated in FIG. 18 includes a step 150 of introducing feed of biological material including adipose tissue into an internal fluid containment space of a portable, single-use container of a portable tissue processing unit. For discussion purposes the processing unit is assumed to include the features of the processing unit 100 as shown and described in relation to FIGS. 1-17, although other processing unit configurations could alternatively be used. During the introducing feed of biological material step 150, biological material including adipose tissue may be introduced through an unsealed inlet port (e.g., inlet port 314) through a top of the container into a tissue retention portion of the internal fluid containment space, and preferably with the tissue processing unit in an upright orientation. The biological material in the internal fluid containment space is subjected to the washing step 152. The washing step 152 may include adding aqueous wash liquid into the internal fluid containment space (e.g., through the unsealed inlet port 314) and mixing the wash liquid and the biological material in the internal fluid containment space to separate blood and other undesirable components from the biological material. The wash liquid and biological material may be mixed by rotating a rotatable mixing assembly (e.g., the rotatable assembly 324) within the internal fluid containment space to mix contents within the internal fluid containment space. Beneficially, the mixing may be performed with the tissue processing unit in an upright orientation. Alternatively, the mixing may be performed by rotational processing of the tissue processing unit in a reclined orientation, in a manner similar to as described above for rotational processing during enzymatic digestion. The washing step 152 may include, following such mixing, removing used wash liquid from the internal fluid containment space, for example by suctioning the wash liquid from a filtrate side of an internal filter in the tissue processing unit (e.g., from the filtrate portion 312) through a suction port of the tissue processing unit (e.g., the suction port 316). The tissue processing unit may beneficially be in the upright orientation when adding the wash liquid to and when removing used wash liquid from the internal fluid containment space. The washing step 152 may include multiple iterations of adding, mixing and removing wash liquid.

Figure 18:
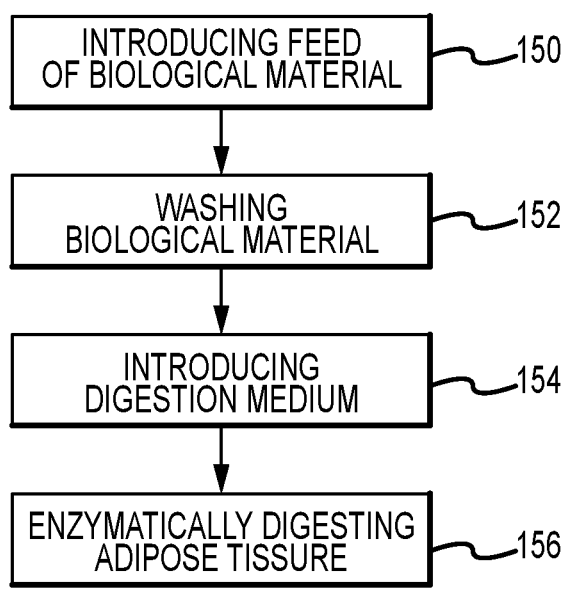
FIG. 18 is a generalized process block diagram illustrating one embodiment of processing for a method for processing biological material including adipose tissue.

As shown in FIG. 18, the illustrated method implementation includes, after the washing step 152, a step 154 of introducing digestion medium into the internal fluid containment space of the tissue processing unit (e.g., through the unsealed inlet port 314 or unsealed additional port 318) to contact the washed biological material in the internal fluid containment space. The tissue processing unit may beneficially be in the upright orientation during the step 154 of adding the digestion medium. In some preferred implementations, the enzyme may be or include collagenase in an amount to provide between about 200 and 300 collagen digestion units (CDU) per milliliter of catalytic volume within the internal fluid containment space of the tissue processing unit, where the catalytic volume equals total volume of the process material mass disposed in the internal fluid containment space for digestion processing, including the combined volumes of the digestion medium and the biological material. In some preferred implementation alternatives, the process fluid mass in the internal fluid containment space of the tissue processing unit following the step 154 is in an amount corresponding with a quiescent partial fill volume with a quiescent headspace volume above the quiescent partial fill volume, as described above.

As shown in FIG. 18, the illustrated method implementation includes, after the introducing digestion medium step 154, a step 156 of enzymatically digesting adipose tissue of the biological material in the internal fluid containment space of the tissue processing unit. Such enzymatically digesting may beneficially include or be preceded by repositioning the tissue processing unit from an upright orientation to a reclined orientation. In some preferred implementations, the enzymatically digesting step 156 may include rotational processing (e.g., driven by the digestion drive unit 200) in which the tissue processing unit is rotated about an axis of rotation (e.g., axis of rotation 102) with the tissue processing unit in the reclined orientation and with the inlet port (e.g. inlet port 314) sealed. In some preferred implementations, the enzymatically digesting step 156 includes mixing the process material mass within the internal fluid containment space including moving one or more mixing blades (e.g., of mixing impeller 326 and/or mixing paddles 340) through periodically repeating mixing cycles in the internal fluid containment space to contact and mix the process material mass. Each such mixing cycle may beneficially include moving at least a portion of one or more such mixing blades sequentially through a quiescent partial fill volume and a quiescent headspace volume, as described above. Such mixing cycles may, for example, be provided by rotations of the tissue processing unit about the axis of rotation, with the rotational speed corresponding to the frequency of the mixing cycles, which may advantageously be at a relatively slow frequency to reduce potential for detrimental entrainment of air and development of froth, as previously described. The enzymatically digesting step 156 may beneficially be performed with the tissue processing unit maintained in a temperature-controlled environment at a temperature close to normal human biological temperature (37° C.), and preferably within a range of from 35° C. to 42° C. Such temperature control may beneficially be provided, for example, by disposing the tissue processing system (e.g., tissue processing system 10) in a temperature-controlled environment, for example in a temperature-controlled oven or incubator unit. Such enzymatic digestion in a temperature-controlled environment may preferably be conducted for a time preferably in a range of from 20 minutes to 120 minutes, and preferably with the tissue processing unit being subjected to the rotational processing for a time of at least 10 minutes, more preferably from 10 minutes to 120 minutes and even more preferably from 20 minutes to 120 minutes.

The processing illustrated in FIG. 18 may also include one or more steps before, after and/or between any of the steps 150, 152, 154 and 156 illustrated in the general processing sequence shown in FIG. 18.

ADDITIONAL CONTEMPLATED IMPLEMENTATION COMBINATIONS

Some other contemplated embodiments of implementation combinations for various aspects of this disclosure, with or without additional features as disclosed above or elsewhere herein, are summarized as follows:

1. A tissue digestion system for dissociation of and release of cellular components from the adipose tissue, the system comprising:
   a portable tissue processing unit for containing biological material including adipose tissue during enzymatic digestion processing to dissociate and release cellular material from the adipose tissue, the tissue processing unit including a single-use processing container with an internal fluid containment space to contain biological material including adipose tissue during enzymatic digestion processing;
   the tissue processing unit comprising:
      an axis of rotation extending through the fluid container in a direction from a bottom of the container toward a top of the container, the tissue processing unit being rotatable about the axis of rotation to rotate the fluid container about the axis of rotation for rotational processing of contents in the internal fluid containment space during the enzymatic digestion processing;
      a selectively sealable and un-sealable inlet port through the top of the container and in fluid communication with the internal fluid containment space;
      an upright orientation for introducing biological material containing adipose tissue from outside of to inside of the internal fluid containment space through the inlet port;
      a reclined orientation for performing the rotational processing, wherein in the reclined orientation the axis of rotation is at a reclined angle to horizontal relative to the upright orientation, and wherein in the reclined orientation the axis of rotation is inclined relative to horizontal at an angle of inclination in a range of from 0° to 45°; and
      at least one mixing blade disposed in the internal fluid containment space of the container to contact and mix contents within the internal fluid containment space during the rotational processing; and
   a digestion drive unit configured to selectively receive the tissue processing unit in the reclined orientation to drive rotation of the tissue processing unit and the container in the reclined orientation about the axis of rotation to mix contents within the internal fluid containment space with the said at least one mixing blade during the rotational processing.

2. The tissue digestion system of combination 1, wherein in the upright orientation the axis of rotation is inclined relative to horizontal at a first angle of inclination in a range of from 60° to 90°.

3. The tissue digestion system of combination 2, wherein the first angle of inclination is in a range of from 75° to 90°.

4. The tissue digestion system of any one of combinations 1-3, wherein the angle of inclination of the axis of rotation in the reclined orientation is in a range of from 0° to 30°, and is optionally at least 2°.

5. The tissue digestion system of combination 4, wherein the angle of inclination of the axis of rotation in the reclined orientation is not larger than 15°, and preferably is in a range of from 2° to 15°.

6. The tissue digestion system of any one of combinations 1-5, wherein the digestion drive unit comprises a plurality of longitudinally-extending rotational drive members on which the tissue processing unit is supported in the reclined orientation when the tissue processing unit is received by the digestion drive unit, each said rotational drive member having a longitudinal axis and being rotatable about the respective longitudinal axis to drive rotation of the tissue processing unit in the reclined orientation about the axis of rotation.

7. The tissue digestion system of combination 6, wherein each said longitudinal axis is parallel to the axis of rotation of the tissue processing unit in the reclined orientation received by the digestion drive unit.

8. The tissue digestion system of either one of combination 6 or combination 7, wherein each said rotational drive member is rotationally mounted in the digestion drive unit adjacent a proximal end of the rotational drive member and each said rotational drive member has a distal end longitudinally opposite the proximal end along the longitudinal axis, and wherein each said rotational drive member has a tapered longitudinal portion on which the cross-section of the rotational drive member tapers along the longitudinal axis in a direction from the proximal end toward the distal end.

9. The tissue digestion system of combination 8, wherein the tapered longitudinal portion is a first longitudinal portion of each said rotational drive member over which a first portion of the tissue processing unit is supported when the tissue processing unit is received in the reclined orientation by the digestion drive unit and each said rotational drive member comprises a second longitudinal portion disposed distally of the first longitudinal portion over which a second portion of the tissue processing unit is supported when the tissue processing unit is received in the reclined orientation by the digestion drive unit; and the cross-section of each said rotational drive member over the second longitudinal portion either tapers at a smaller rate of taper than over the first longitudinal portion or is constant over the second longitudinal portion.

10. The tissue digestion system of any one of combinations 6-9, wherein the digestion drive unit comprises a rotational drive motor and a rotational drive connection between the rotational drive motor and at least one said rotational drive member to drive rotation of the at least one said rotational drive member about the respective longitudinal axis to drive rotation of the tissue processing unit in the reclined orientation about the axis of rotation.

11. The tissue digestion system of combination 10, wherein at least one rotational drive member includes at least 2 said rotational drive members connected with the rotational drive connection to drive rotation of the at least 2 said rotational drive members about their respective longitudinal axes to drive rotation of the tissue processing unit in the reclined orientation about the axis of rotation.

12. The tissue digestion system of combination 11, wherein the rotation drive connection comprises a drive belt connected to the at least two rotational drive members and to a rotational output shaft of the rotational drive motor.

13. The tissue digestion system of any one of combinations 10-12, wherein the digestion drive unit comprises an off mode when the rotational drive motor is not operating to drive rotation of any said rotational drive member and an on mode when the rotational drive motor is operating to drive rotation of the at least one said rotational drive member to drive rotation of the tissue processing unit in the reclined position received by the digestion drive unit at a rotational speed in a range of from 5 to 40 revolutions per minute about the axis of rotation.

14. The tissue digestion system of combination 13, wherein the digestion drive unit comprises a user actuatable on-off switch to switch the digestion drive unit between the on mode and the off mode.

15. The tissue digestion system of either one of combination 13 or combination 14, wherein the on mode operates at a set rotational speed within the range that is not user-adjustable.

16. The tissue digestion system of either one of combination 13 or combination 14, wherein the digestion drive unit comprises a user-manipulable adjustment mechanism to adjust the rotational speed within the range.

17. The tissue digestion system of any one of combinations 6-16, wherein a said rotational drive member comprises a traction feature extending circumferentially around the said rotational drive member and rotated about the longitudinal axis with rotation of the said rotational drive member about the longitudinal axis; and the traction feature is of a material having a hardness in a range of from Shore A durometer 30 to Shore A durometer 90 in contact with an outside surface of the tissue processing unit when the tissue processing unit is received in the reclined orientation by the digestion drive unit.

18. The tissue digestion system of combination 17, wherein the said rotational drive member comprises a structural portion made of a first material of construction and the material of the traction feature is a second material of construction, and the first material of construction is a harder material than the second material of construction.

19. The tissue digestion system of combination 18, wherein the first material of construction is a metallic material and the second material of construction is an elastomeric material.

20. The tissue digestion system of either one of combination 18 or combination 19, wherein the traction feature is in the form of a circumferential ring supported on the structural portion.

21. The tissue digestion system of combination 20, wherein the ring is retained in a circumferential recess in the structural portion.

22. The tissue digestion system of any one of combinations 17-21, wherein at least two said rotational drive members each includes a said traction feature.

23. The tissue digestion system of any one of combinations 1-22, wherein as received in the reclined orientation by the digestion drive unit, the tissue processing unit has a top portion that is not in contact with any portion of the digestion drive unit.

24. The tissue digestion system of any one of combinations 1-23, wherein:

the tissue processing unit comprises a protective processing sleeve and a container apparatus including the container removably received in the processing sleeve with the bottom of the container apparatus disposed inside of and toward a bottom of the processing sleeve and with the processing sleeve having an open top not blocking access to the top of the container;

the container apparatus is selectively removable from the processing sleeve; and as the tissue processing unit is received by the digestion drive unit in the reclined orientation, the processing sleeve is in contact with the digestion drive unit.

25. The tissue digestion system of combination 24, wherein as the tissue processing unit is received by the digestion drive unit in the reclined orientation, the tissue processing unit is in contact with the digestion drive unit only through surfaces of the processing sleeve and no portion of the container apparatus contacts any portion of the digestion drive unit.

26. The tissue digestion system of either one of combination 24 or combination 25, wherein:

the container apparatus comprises a container lid at the top of the container that encloses the internal fluid containment space from above when the tissue processing unit is in the upright orientation;

the fluid container comprise a lip around a top portion of the container apparatus; and in the upright orientation the container lid projects above the top of the processing sleeve and the lip is disposed above the top of the processing sleeve and projects laterally to a side of a top edge of the processing sleeve.

27. The tissue digestion system of combination 26, wherein the container apparatus has a maximum cross-dimension between opposing lateral edges of the lip in a range of from 40 millimeters to 140 millimeters and the lip extends laterally beyond the top edge of the processing sleeve by at least 1 millimeter.

28. The tissue digestion system of any one of combinations 1-27, wherein as received by the digestion drive unit in the reclined orientation, the digestion drive unit supports the tissue processing unit only through contact of the digestion drive unit with outside surfaces of side portions of the tissue processing unit having a circular cross-section perpendicular to the axis of rotation.

29. The tissue digestion system of any one of combinations 1-28, wherein the container comprises an internal filter disposed within the internal fluid containment space and the internal fluid containment space comprises a tissue retention portion disposed on one side of the filter and configured to receive feed of biological material introduced through the inlet port and a filtrate portion disposed on an opposing side the filter to receive fluid passing from the tissue retention portion across the filter and into the filtrate portion.

30. The tissue digestion system of combination 29, wherein the container comprises a vacuum suction port in fluid communication with the filtrate portion of the internal fluid containment space to suction liquid from the filtrate portion.

31. The method of any one of combinations 1-28, wherein the container has a maximum fluid fill volume capacity within the internal fluid containment space in a range of from 40 milliliters to 500 milliliters.

32. The tissue digestion system of any one of combinations 29-31, wherein each said mixing blade is disposed in the tissue retention portion and is connected with a mixing shaft extending through a wall of the container from outside of to inside of the internal fluid containment space, and the mixing shaft is rotatable relative to the container to rotate each said mixing blade through the tissue retention portion of the internal fluid containment space.

33. The tissue digestion system of combination 32, wherein a longitudinal axis of the mixing shaft is coincident with or parallel to the axis of rotation.

34. The tissue digestion system of either one of combination 32 or combination 33, wherein the tissue processing unit comprises a handle disposed outside of the internal fluid containment space and connected with the mixing shaft, the handle being hand-manipulable to rotate the mixing shaft relative to the container to rotate each said mixing blade through the tissue retention portion of the internal fluid containment space.

35. The tissue digestion system of any one of combinations 32-34, wherein the tissue processing unit is configured with the mixing shaft and container retained in fixed relation as the tissue processing unit is rotated by the digestion drive unit about the axis of rotation in the reclined orientation.

36. The tissue digestion system of any one of combinations 1-35, wherein the container and each said mixing blade rotate together as a unit as the tissue processing unit is rotated by the digestion drive unit during the rotational processing about the axis of rotation in the reclined orientation.

37. The tissue digestion system of any one of combinations 1-36, comprising the tissue processing unit received in the digestion drive unit in the reclined orientation.

38. The tissue digestion system of combination 37, comprising a process material mass disposed in the internal fluid containment space, wherein the process material mass comprises biological material including adipose tissue and enzyme for enzymatic digestion of the adipose tissue, and the process material mass is in an amount having a quiescent volume corresponding to a quiescent partial fill volume of the internal fluid containment space in a range of from 30 percent to 75 percent of a maximum fluid fill volume capacity of the internal fluid containment space with a quiescent headspace volume in the internal fluid containment space above the quiescent partial fill volume, and wherein the quiescent headspace volume is in a range of from 25 percent to 70 percent of the maximum fluid fill volume capacity.

39. The tissue digestion system of combination 38, wherein the quiescent partial fill volume has a first vertical height in the internal fluid containment space and the quiescent headspace has a second vertical height in the internal fluid containment space above the quiescent partial fill volume; and a ratio of the second vertical height to the first vertical height is in a range of from 1.4:1 to 0.3:1.

40. The tissue digestion system of combination 39 wherein a sum of the first vertical height and the second vertical height is in a range of from 40 millimeters to 140 millimeters.

41. The tissue digestion system of any one of combinations 38-40, wherein: a said mixing blade is disposed with at least a portion of the mixing blade to move through periodically repeating mixing cycles in the internal fluid containment space to contact and mix the process material mass as the tissue processing unit is rotated by the digestion drive unit about the axis of rotation in the reclined orientation; and each said mixing cycle comprises moving the at least a portion of the mixing blade sequentially through the quiescent partial fill volume and the quiescent headspace volume.

42. The tissue digestion system of combination 41, wherein a plurality of said mixing blades are each disposed with a said at least a portion of each one of the plurality of said mixing blades to move through said periodically repeating mixing cycles in the internal fluid containment space to contact and mix the process material mass as the tissue processing unit is rotated by the digestion drive unit about the axis of rotation in the reclined orientation.

43. The tissue digestion system of any one of combinations 37-42, wherein the digestion drive unit is rotating the tissue processing unit in the reclined orientation about the axis of rotation.

44. The tissue digestion system of any one of combinations 37-42, wherein the digestion drive unit is rotating the tissue processing unit in the reclined orientation about the axis of rotation at a rotational speed in a range of from 5 to 40 revolutions.

45. A method for processing biological material including adipose tissue to dissociate and release cellular components from the adipose tissue, the method comprising:

introducing a digestion medium into an internal fluid containment space of a portable, single-use container of a portable tissue processing unit to contact biological material including adipose tissue in the internal fluid containment space, wherein the digestion medium includes enzyme for enzymatic digestion of the adipose tissue and wherein the tissue processing unit comprises:

an axis of rotation extending through container in a direction from a bottom of the container toward a top of the container, the tissue processing unit and the container being rotatable about the axis of rotation for rotational processing of contents in the internal fluid containment space;

at least one selectively sealable and un-sealable inlet port through the top of the container and in fluid communication with the internal fluid containment space; and an upright orientation and a reclined orientation, wherein in the reclined orientation the axis of rotation is at a reclined angle to horizontal relative to the upright orientation and wherein in the reclined orientation the axis of rotation is inclined relative to horizontal at an angle of inclination in a range of from 0° to 45°;

during the introducing the digestion medium, the tissue processing unit is in the upright orientation and the digestion medium is introduced into the internal fluid containment space through an unsealed said inlet port;

after the introducing the digestion medium, enzymatically digesting adipose tissue of the biological material in the internal fluid containment space in the presence of the enzyme in the internal fluid containment space, comprising rotating the tissue processing unit and the container about the axis of rotation while the tissue processing unit is in the reclined orientation with the said inlet port sealed.

46. The method of combination 45, comprising prior to the introducing the digestion medium:

introducing feed of the biological material including adipose tissue into the internal fluid containment space through an unsealed said inlet port while the tissue processing unit is in the upright orientation.

47. The method of either one of combination 45 and combination 46, wherein after completion of the introducing the digestion medium, the biological material and the digestion medium in the internal fluid containment space are in a process material mass in the internal containment space, wherein the process material mass is in an amount having a quiescent volume corresponding to a quiescent partial fill volume of the internal fluid containment space in a range of from 30 percent to 75 percent of a maximum fluid fill volume capacity of the internal fluid containment space with a quiescent headspace volume in the internal fluid containment space above the quiescent partial fill volume, wherein the quiescent headspace volume is in a range of from 25 percent to 70 percent of the maximum fluid fill volume capacity.

48. A method for processing biological material including adipose tissue to dissociate and release cellular components from the adipose tissue, the method comprising:

introducing feed of biological material including adipose tissue into an internal fluid containment space of a portable, single-use container of a portable tissue processing unit, wherein the tissue processing unit comprises:

an axis of rotation extending through the container in a direction from a bottom of the container toward a top of the container, the tissue processing unit and the container being rotatable about the axis of rotation for rotational processing of contents in the internal fluid containment space;

at least one selectively sealable and un-sealable inlet port through the top of the container and in fluid communication with the internal fluid containment space; and an upright orientation and a reclined orientation, wherein in the reclined orientation the axis of rotation is at a reclined angle to horizontal relative to the upright orientation and wherein in the reclined orientation the axis of rotation is inclined relative to horizontal at an angle of inclination in a range of from 0° to 45°;

during the introducing a feed of biological material, the tissue processing unit is in the upright orientation and the feed of the biological material is introduced into the internal fluid containment space through an unsealed said inlet port;

after the introducing, enzymatically digesting adipose tissue of the biological material in the internal fluid containment space in the presence of an enzyme in the internal fluid containment space, comprising rotating the tissue processing unit and the container about the axis of rotation while the tissue processing unit is in the reclined orientation with the said inlet port sealed.

49. The method of combination 48, comprising after the introducing the feed of the biological material and before the enzymatically digesting:

introducing a digestion medium comprising the enzyme into the internal fluid containment space through an unsealed said inlet port while the tissue processing unit is in the upright orientation.

50. The method of either one of combination 48 or combination 49, wherein after completion of the introducing the digestion medium, the biological material and the digestion medium in the internal fluid containment space are in a process material mass in the internal containment space, wherein the process material mass is in an amount having a quiescent volume corresponding to a quiescent partial fill volume of the internal fluid containment space in a range of from 30 percent to 75 percent of a maximum fluid fill volume capacity of the internal fluid containment space with a quiescent headspace volume in the internal fluid containment space above the quiescent partial fill volume, wherein the quiescent headspace volume is in a range of from 25 percent to 75 percent of the maximum fluid fill volume capacity.

51. A method for processing biological material including adipose tissue to dissociate and release cellular components from the adipose tissue, the method comprising:

disposing a process fluid mass in an internal fluid containment space of a portable, single-use container of a portable tissue processing unit, the process material mass comprising biological material including adipose tissue and enzyme for enzymatic digestion of the adipose tissue in an internal fluid containment space, wherein the tissue processing unit comprises at least one mixing blade disposed in the internal fluid containment space; and after the disposing, enzymatically digesting the adipose tissue of biological material in the process material mass in the internal fluid containment space, the enzymatically digesting comprising:

mixing the process material mass within the internal fluid containment space, the mixing comprising moving a said mixing blade through periodically repeating mixing cycles in the internal fluid containment space to contact and mix the process fluid mass;

wherein during the mixing the process material mass is in an amount having a quiescent volume corresponding to a quiescent partial fill volume of the internal fluid containment space in a range of from 30 percent to 75 percent of a maximum fluid fill volume capacity of the internal fluid containment space with a quiescent headspace volume in the internal fluid containment space above the quiescent partial fill volume, wherein the quiescent headspace volume is in a range of from 25 percent to 75 percent of the maximum fluid fill volume capacity of the internal fluid containment space; and wherein each said mixing cycle comprises moving at least a portion of the said mixing blade sequentially through the quiescent partial fill volume and the quiescent headspace volume.

52. The method of combination 51, wherein the mixing comprises repeating the mixing cycles at a frequency in a range of from 5 to 40 said mixing cycles per minute.

53. The method of either one of combination 51 or combination 52, wherein the quiescent partial fill volume has a first vertical height in the internal fluid containment space and the headspace has a second vertical height in the internal fluid containment space above the quiescent partial fill volume; and a ratio of the second vertical height to the first vertical height is in a range of from 1.4:1 to 0.3:1.

54. The method of combination 53 wherein a sum of the first vertical height and the second vertical height is in a range of from 40 millimeters to 140 millimeters.

55. The method of any one of combinations 51-54, wherein the maximum fluid fill volume capacity is in a range of from 40 milliliters to 500 milliliters.

56. The method of any one of combinations 51-55, wherein the mixing comprises rotating the said blade about an axis of rotation, wherein during the rotating the axis of rotation is at an angle of inclination relative to horizontal in a range of from 0° to 45°.

57. The method of combination 56, wherein during the rotating the angle of inclination relative to horizontal is no larger than 30°, preferably no larger than 15°, and preferably at least 2°.

58. The method of either one of combination 56 or combination 57, wherein the mixing comprises rotating the tissue processing unit about the axis of rotation.

59. The method of any one of combinations 51-55, wherein:

the tissue processing unit comprises:
an axis of rotation extending through container in a direction from a bottom of the container toward a top of the container, the tissue processing unit and the container being rotatable about the axis of rotation for rotational processing of contents of the container;
at least one selectively sealable and un-sealable inlet port through the top of the container and in fluid communication with the internal fluid containment space; and
an upright orientation and a reclined orientation, wherein in the reclined orientation the axis of rotation is at a reclined angle to horizontal relative to the upright orientation and wherein in the reclined orientation the axis of rotation is inclined relative to horizontal at an angle of inclination in a range of from 0° to 45°;

the method further comprises prior to the enzymatically digesting:
introducing a digestion medium including the enzyme into the internal fluid containment space to contact the biological material including adipose tissue in the internal fluid containment space, and wherein during the introducing the digestion medium the tissue processing unit is in the upright orientation and the digestion medium is introduced into the internal fluid containment space through an unsealed said inlet port.

60. The method of combination 59, wherein the enzymatically digesting comprises rotating the tissue processing unit about the axis of rotation while the tissue processing unit is in the reclined orientation with the said inlet port sealed.

61. The method of any one of combinations 45-50 and 60, comprising prior to the rotating and with the biological material in the internal containment space in contact with the enzyme:
repositioning the tissue processing unit from the upright orientation to the reclined orientation.

62. The method of any one of combinations 45-50, 60 and 61, wherein in the upright orientation the axis of rotation is at a first angle of inclination relative to horizontal in a range of from 60° to 90° and in the reclined orientation the axis of rotation is at a second angle of inclination relative to horizontal in the range of from 0° to 45°, preferably from 0° to 30°.

63. The method of combination 62, wherein the first angle of inclination is in a range of from 75° to 90° relative to horizontal.

64. The method of either one of combination 62 or combination 63, wherein the second angle of inclination is at least 2°.

65. The method of any one of combinations 62-64, wherein the second angle of inclination is not larger than 15°.

66. The method of any one of combinations 62-65, wherein the second angle of inclination is in a range of from 2° to 15°.

67. The method of any one of combinations 45-50 and 60-66, wherein the rotating is at a rotational speed of from 5 to 40 revolutions per minute of the tissue processing unit about the axis of rotation.

68. The method of combination 67, wherein the rotating at the rotational speed is performed for a time period in a range of from 10 minutes to 120 minutes.

69. The method of any one of combinations 45-50 and 60-68, wherein during the rotating, the tissue processing unit is received in the reclined orientation in a digestion drive unit that drives rotation of the tissue processing unit during the rotating.

70. The method of combination 69, wherein as received in the reclined orientation in the digestion drive unit during the rotating, the tissue processing unit is in contact with at least one rotational drive member of the digestion drive unit that drives rotation of tissue processing unit during the rotating.

71. The method of combination 70, wherein during the rotating each said rotational drive member is in peripheral contact with the tissue processing unit and the container is rotating in a first rotational direction that is opposite to a second rotational direction in which each said rotational drive member is rotating.

72. The method of combination 71, wherein as received in the reclined orientation in the digestion drive unit during the rotating, the tissue processing unit rests on a plurality of said rotational drive members.

73. The method of any one of combinations 45-50 and 60-72, comprising prior to the enzymatically digesting, washing the biological material in the internal fluid containment space, the washing comprising:

adding aqueous wash liquid into the internal fluid containment space and mixing the wash liquid and the biological material in the internal fluid containment space; and after the mixing, suctioning used said wash liquid from the internal fluid containment space.

74. The method of combination 73, wherein:
the tissue processing unit comprises a filter disposed in the container separating the internal fluid containment space into a tissue retention portion disposed on one side of the filter and a filtrate portion disposed on another side of the filter and wherein prior to the washing the biological material is disposed in the tissue retention portion of the internal containment space; and
the suctioning comprises suctioning the used said wash liquid from the filtrate portion of the internal fluid containment space.

75. The method of either one combination 73 or combination 74, wherein during the adding the wash liquid and during the suctioning, the tissue processing unit is in the upright orientation.

76. The method of any one of combinations 45-75, wherein the tissue processing unit is as provided in any one of combinations 1-44.

77. The method of any one of combinations 45-76, wherein the enzymatically digesting is performed in the tissue digestion system of any one of combinations 1-44 and comprises the rotational processing.

EXAMPLE

Dissociation of adipose tissue is compared between enzymatic digestion processing agitation performed using an orbital shaker versus reclined rotational processing in a tissue digestion system similar to that shown and described in relation to FIGS. 1-17. All tests are performed with a mixture of washed lipoaspirate and digestion medium with collagenase contained within the internal fluid containment space of a tissue processing unit similar to that shown and described in FIGS. 1-17. Orbital shaker tests are performed with the tissue processing unit in an upright orientation subjected to orbital shaking at a speed of 150 revolutions per minute and rotational processing tests are performed with the tissue processing unit in a reclined orientation received by the digestion drive unit with an angle of inclination of the axis of rotation at 6° relative to horizontal (in an orientation similar to as shown in FIG. 2) at a rotational speed of about 22 revolutions per minute. In both cases, agitation is performed in a temperature controlled environment maintained at about 38° C. The container of the tissue processing unit has a maximum fluid fill volume capacity of about 350 milliliters and during the digestion processing the internal fluid containment space is partially filled with a process material mass (washed biological material plus digestion medium) having a combined volume (quiescent partial fill volume) of about 205 milliliters, occupying about 59% of the maximum fluid fill volume capacity.

The tests are performed as follows:
1. Warm a batch of lipoaspirate in an initial canister to at least 37° C. in an incubator unit.
2. Wash the lipoaspirate as follows to remove blood and fluids:
   a. Decant lipoaspirate in the canister for 10 minutes
   b. Using a suction tube, aspirate infranatant fluids from the canister
   c. Add warmed Lactated Ringer's Solution at 37° C., mix well
   d. Repeat wash cycle (steps a, b, c) 3 times
3. Remove washed lipoaspirate from the initial canister in 60 cc catheter tip syringes.
4. Aliquot 50-60 cc of washed lipoaspirate into the internal fluid containment space of each tissue processing unit, 10 ml at a time, moving from device to device, to maximally homogenize the adipose in each tissue processing unit.
5. Precisely weigh each tissue processing unit to determine final weight.
6. Add warm Lactated Ringer's Solution to obtain the desired quiescent partial fill volume in the internal fluid containment space of each tissue processing unit. Stir.
7. Add 5 cc of enzyme suspension (50,000 CDU) to each tissue processing unit (providing approximately 250 CDUs per milliliter of catalytic volume). Stir in with the manual rotary mixer.
8. Place in respective orbital shaker in upright orientation or digestion drive unit in reclined orientation for rotational processing for a fixed period of time.
9. Balance the tissue processing units to within 5 grams of each other through addition of Lactated Ringer's Solution as needed to the internal fluid containment spaces of the respective tissue processing units.
10. Centrifuge balanced pairs of the tissue processing units at 600 g's (gravity units) for 6 minutes.
11. Stir each tissue processing unit for 10 seconds with the manual rotary mixer.
12. Centrifuge again at 600 g's for 4 minutes.
13. Aspirate each resulting cell pellet from the pellet well of each tissue processing unit directly into a 5 cc collection syringe to resuspend the material of the cell pellet in 1 cc of Lactated Ringer's Solution preloaded into the collection syringe.
14. Record final volume of syringe suspension from each tissue processing unit.
15. Attach 5 cc mixing syringe to each collection syringe. Mix the suspension by making 5 passes between the collection syringe and mixing syringe.
16. Take a sample of the suspension from each collection syringe, 6 drops in a 1.5 ml Eppendorf sample tube. Add 6 drops of Lactated Ringer's Solution to form a dilution ratio of 2.
17. Shake Eppendorf tube, complete a cell count on each sample with a nucleated cell counter.

For each agitation method (orbital shaker or rotational processing), tests are run both with 40 minutes of agitation in step 8 and with 50 minutes of agitation in step 8.

Results are summarized in Table 1.

TABLE 1

| Test | #1 Upright Orbital 40 min | #2 Upright Orbital 50 min | #3 Reclined Rotational 40 min | #4 Reclined Rotational 50 min |
|---|---|---|---|---|
| Dry weight of processing unit (grams) | 161 | 161 | 161 | 161 |
| Wet weight processing unit with washed adipose tissue (grams) | 224 | 216 | 214 | 212 |
| Dry adipose weight, by difference (grams) | 63 | 55 | 53 | 51 |

TABLE 1-continued

| Test | #1 Upright Orbital 40 min | #2 Upright Orbital 50 min | #3 Reclined Rotational 40 min | #4 Reclined Rotational 50 min |
|---|---|---|---|---|
| Total cells recovered | 8.82E+06 | 7.60E+06 | 3.75E+07 | 5.64E+07 |
| Cells recovered per gram of adipose | 1.40E+05 | 1.38E+05 | 7.08E+05 | 1.11E+06 |

Tests #1 and #3 compare results of the upright orbital shaker agitation vs reclined rotational agitation for 40 minutes, and show about a 400% improvement in cells recovered per gram of adipose tissue in the lipoaspirate samples tested using the reclined rotational processing approach relative to the upright orbital shaker approach. Tests #2 and #4 compare results of the orbital shaker agitation vs reclined rotational agitation for 50 minutes, showing about a 700% improvement in cells recovered per gram of adipose tissue in the lipoaspirate samples tested using the reclined rotational processing approach relative to the upright orbital shaker approach. Notably, increasing digestion agitation time from 40 to 50 minutes resulted in no improvement in cell recovery per gram of adipose in the case of upright orbital agitation (Test #2 vs Test #1), whereas cell recovery per gram of adipose increased by about 57% with the increased agitation time in the case of reclined rotational processing (Test #4 vs Test #3), indicating that in the orbital agitation case, effective penetration of the enzyme into the biological material and dissociation of the adipose has essentially stopped before completion of 40 minutes of agitation and is not improved with the longer agitation time, whereas with the reclined rotational agitation the enzyme appears to continue to penetrate into the adipose to contact and dissociate additional adipose tissue during the extended agitation period. The improved cell recovery per gram of adipose using rotational agitation of the tissue processing unit in a reclined orientation during enzymatic digestion relative to orbital agitation in an upright orientation is significant and striking in the magnitude of improvement.

The foregoing description of the present invention and various aspects thereof has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

The description of a feature or features in a particular combination do not exclude the inclusion of an additional feature or features in a variation of the particular combination. Processing steps and sequencing are for illustration only, and such illustrations do not exclude inclusion of other steps or other sequencing of steps to an extent not necessarily incompatible. Additional steps may be included between any illustrated processing steps or before or after any illustrated processing step to an extent not necessarily incompatible.

The terms "comprising", "containing", "including" and "having", and grammatical variations of those terms, are intended to be inclusive and nonlimiting in that the use of such terms indicates the presence of a stated condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or any appropriate grammatical variation of such narrower terms). For example, a statement that something "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all.

What is claimed is:

1. A method for processing biological material including adipose tissue to dissociate the adipose tissue and release cellular components from the adipose tissue for preparation of stromal vascular fraction, the method comprising:

introducing an aqueous digestion medium into an internal fluid containment space of a portable, single-use processing container of a portable tissue processing unit to contact biological material including adipose tissue in the internal fluid containment space, wherein the digestion medium includes enzyme for enzymatic digestion of the adipose tissue and wherein the tissue processing unit comprises:

an axis of rotation extending through the processing container in a direction from a bottom of the processing container toward a top of the container, the tissue processing unit and the processing container being rotatable about the axis of rotation for rotational processing of contents in the internal fluid containment space;

at least one selectively sealable and un-sealable inlet port through the top of the processing container and in fluid communication with the internal fluid containment space;

an upright orientation and a reclined orientation, wherein in the reclined orientation the axis of rotation is at a reclined angle to horizontal relative to the upright orientation and wherein in the reclined orientation the axis of rotation is inclined relative to horizontal at an angle of inclination in a range of from 0° to 45°; and at least one mixing blade disposed in the internal fluid containment space of the processing container;

during the introducing the digestion medium, the tissue processing unit is in the upright orientation and the digestion medium is introduced into the internal fluid containment space through an unsealed said inlet port;

after the introducing the digestion medium, enzymatically digesting the adipose tissue of the biological material in the internal fluid containment space in presence of the enzyme in the internal fluid containment space to dissociate the adipose tissue and release cells of stromal vascular fraction from the adipose tissue, comprising rotating the tissue processing unit and the processing container about the axis of rotation while the tissue processing unit is in the reclined orientation with the said inlet port sealed;

after the introducing the digestion medium and prior to the rotating, repositioning the tissue processing unit from the upright orientation to the reclined orientation with the biological material and the digestion medium in a process material mass in the internal fluid containment space in the reclined orientation, wherein in the reclined orientation the process material mass is in an amount having a quiescent volume corresponding to a quiescent partial fill volume of the internal fluid containment space with a quiescent headspace volume in the internal fluid containment space above the quiescent partial fill volume; and the rotating the tissue processing unit and the processing container comprising:
rotating the processing container and the at least one mixing blade together as a unit and not relative to each other; and
during the rotating the processing container and the at least one mixing blade together as a unit and not relative to each other, moving the at least one mixing blade through periodically repeating mixing cycles in the internal fluid containment space to contact and mix the process fluid mass, wherein each said mixing cycle comprises moving at least a portion of the at least one mixing blade sequentially through the quiescent partial fill volume and the quiescent headspace volume.

2. The method of claim 1, comprising prior to the introducing the digestion medium:
introducing feed of the biological material including adipose tissue into the internal fluid containment space through an unsealed said inlet port while the tissue processing unit is in the upright orientation.

3. The method of claim 1, wherein the quiescent partial fill volume of the internal fluid containment space in a range of from 30 percent to 75 percent of a maximum fluid fill volume capacity and the quiescent headspace volume is in a range of from 25 percent to 70 percent of the maximum fluid fill volume capacity.

4. The method of claim 1, wherein in the upright orientation the axis of rotation is at a first angle of inclination relative to horizontal in a range of from 60° to 90° and in the reclined orientation the axis of rotation is at a second angle of inclination relative to horizontal in the range of from 0° to 30°.

5. The method of claim 4, wherein the first angle of inclination is in a range of from 75° to 90° relative to horizontal; and
the second angle of inclination is not larger than 15°.

6. The method of claim 4, wherein the rotating is at a rotational speed of from 5 to 40 revolutions per minute of the tissue processing unit about the axis of rotation; and
the rotating at the rotational speed is performed for a time period in a range of from 10 minutes to 120 minutes.

7. The method of claim 4, comprising prior to the enzymatically digesting, washing the biological material in the internal fluid containment space, the washing comprising:
adding aqueous wash liquid into the internal fluid containment space and mixing the wash liquid and the biological material in the internal fluid containment space;
after the mixing, suctioning used said wash liquid from the internal fluid containment space; and
during the adding the wash liquid and during the suctioning, the tissue processing unit is in the upright orientation.

8. The method of claim 1, wherein:
during the rotating, the tissue processing unit is received in the reclined orientation in a digestion drive unit that drives rotation of the tissue processing unit during the rotating;
as received in the reclined orientation in the digestion drive unit during the rotating, the tissue processing unit is in contact with at least one rotational drive member of the digestion drive unit that drives rotation of tissue processing unit during the rotating; and
during the rotating the at least one rotational drive member is in peripheral contact with the tissue processing unit and the processing container is rotating in a first rotational direction that is opposite to a second rotational direction in which the at least one rotational drive member is rotating.

9. The method of claim 1, wherein the quiescent partial fill volume has a first vertical height in the internal fluid containment space and the headspace has a second vertical height in the internal fluid containment space above the quiescent partial fill volume;
a ratio of the second vertical height to the first vertical height is in a range of from 1.4:1 to 0.3:1; and
a sum of the first vertical height and the second vertical height is in a range of from 40 millimeters to 140 millimeters.

10. The method of claim 3, wherein the maximum fluid fill volume capacity is in a range of from 40 milliliters to 500 milliliters.

11. The method of claim 1, wherein at commencement of the rotating the processing container and the at least one mixing blade together as a unit and not relative to each other:
the process material mass comprises multiple separate material phases including a first material phase comprising the adipose tissue and a second material phase comprising a liquid phase of the digestion medium.

12. The method of claim 11, wherein at commencement of the rotating the processing container and the at least one mixing blade together as a unit and not relative to each other:
a portion of the second material phase is disposed in a first portion of the quiescent partial fill volume above a second portion of the quiescent partial fill volume comprising at least a portion of the first material phase.

13. The method of claim 12, wherein the mixing cycle comprises moving the at least a portion of the at least one mixing blade from the quiescent headspace volume through the first portion of the quiescent partial fill volume and into the second portion of the quiescent partial fill volume.

14. The method of claim 13, wherein the rotating the processing container and the at least one mixing blade together as a unit and not relative to each other comprises:
the at least one mixing blade pulling a portion of the digestion medium from the first portion of the quiescent partial fill volume into at least a portion of the adipose tissue in the second portion of the quiescent partial fill volume.

15. A method for processing biological material including adipose tissue to dissociate and release cellular components from the adipose tissue, the method comprising:
    introducing a digestion medium into an internal fluid containment space of a portable, single-use processing container of a portable tissue processing unit to contact biological material including adipose tissue in the internal fluid containment space, wherein the digestion medium includes enzyme for enzymatic digestion of the adipose tissue and wherein the tissue processing unit comprises:
        an axis of rotation extending through the processing container in a direction from a bottom of the processing container toward a top of the container, the tissue processing unit and the processing container being rotatable about the axis of rotation for rotational processing of contents in the internal fluid containment space;
        at least one selectively sealable and un-sealable inlet port through the top of the processing container and in fluid communication with the internal fluid containment space; and
        an upright orientation and a reclined orientation, wherein in the reclined orientation the axis of rotation is at a reclined angle to horizontal relative to the upright orientation and wherein in the reclined orientation the axis of rotation is inclined relative to horizontal at an angle of inclination in a range of from 0° to 45°;
    during the introducing the digestion medium, the tissue processing unit is in the upright orientation and the digestion medium is introduced into the internal fluid containment space through an unsealed said inlet port;
    after the introducing the digestion medium, enzymatically digesting adipose tissue of the biological material in the internal fluid containment space in presence of the enzyme in the internal fluid containment space, comprising rotating the tissue processing unit and the processing container about the axis of rotation while the tissue processing unit is in the reclined orientation with the said inlet port sealed;
    and wherein:
        during the rotating, the tissue processing unit is received in the reclined orientation in a digestion drive unit that drives rotation of the tissue processing unit during the rotating;
        as received in the reclined orientation in the digestion drive unit during the rotating, the tissue processing unit is in contact with at least one rotational drive member of the digestion drive unit that drives rotation of tissue processing unit during the rotating; and
        during the rotating the at least one rotational drive member is in peripheral contact with the tissue processing unit and the processing container is rotating in a first rotational direction that is opposite to a second rotational direction in which the at least one rotational drive member is rotating; and
        as received in the reclined orientation in the digestion drive unit during the rotating, the tissue processing unit rests on a plurality of said rotational drive members.

16. A method for processing biological material including adipose tissue to dissociate and release cellular components from the adipose tissue, the method comprising:
    introducing a digestion medium into an internal fluid containment space of a portable, single-use processing container of a portable tissue processing unit to contact biological material including adipose tissue in the internal fluid containment space, wherein the digestion medium includes enzyme for enzymatic digestion of the adipose tissue and wherein the tissue processing unit comprises:
        an axis of rotation extending through the processing container in a direction from a bottom of the processing container toward a top of the container, the tissue processing unit and the processing container being rotatable about the axis of rotation for rotational processing of contents in the internal fluid containment space;
        at least one selectively sealable and un-sealable inlet port through the top of the processing container and in fluid communication with the internal fluid containment space; and
        an upright orientation and a reclined orientation, wherein in the reclined orientation the axis of rotation is at a reclined angle to horizontal relative to the upright orientation and wherein in the reclined orientation the axis of rotation is inclined relative to horizontal at an angle of inclination in a range of from 0° to 45°:
    during the introducing the digestion medium, the tissue processing unit is in the upright orientation and the digestion medium is introduced into the internal fluid containment space through an unsealed said inlet port;
    after the introducing the digestion medium, enzymatically digesting adipose tissue of the biological material in the internal fluid containment space in presence of the enzyme in the internal fluid containment space, comprising rotating the tissue processing unit and the processing container about the axis of rotation while the tissue processing unit is in the reclined orientation with the said inlet port sealed;
    and wherein;
        during the rotating, the tissue processing unit is received in the reclined orientation in a digestion drive unit that drives rotation of the tissue processing unit during the rotating;
        the digestion drive unit comprises at least one rotational drive member that drives rotation of the tissue processing unit during the rotating;
        as received in the reclined orientation in the digestion drive unit during the rotating, the tissue processing unit is in contact with the at least one rotational drive member; and
        during the rotating the at least one rotational drive member is in peripheral contact with the tissue processing unit and the processing container is rotating in a first rotational direction that is opposite to a second rotational direction in which the at least one rotational drive member is rotating;
        the at least one rotational drive member is rotationally mounted in the digestion drive unit adjacent a proximal end of the at least one rotational drive member and the at least one rotational drive member has a distal end longitudinally opposite the proximal end; and
        during the rotating a top portion of the tissue processing unit extends beyond the distal end of the at least one rotational drive member.

17. The method of claim 16, wherein the at least one rotational drive member has a tapered longitudinal portion on which a cross-section of the at least one rotational drive member tapers in a longitudinal direction from the proximal end toward the distal end.

18. The method of claim 17, wherein:
the at least one rotational drive member comprises a traction feature extending circumferentially around the at least one rotational drive member and the traction feature rotates with rotation of the at least one rotational drive member during the rotating; and
the traction feature is of a material having a hardness in a range of from Shore A durometer 30 to Shore A durometer 90 in contact with an outside surface of the tissue processing unit during the rotating.

19. The method of claim 18, wherein:
the tapered longitudinal portion is a first longitudinal portion of the at least one rotational drive member over which a first portion of the tissue processing unit is supported during the rotating and the at least one rotational drive member comprises a second longitudinal portion disposed distally of the first longitudinal portion over which a second portion of the tissue processing unit is supported during the rotating;
the cross-section of the at least one rotational drive member over the second longitudinal portion either tapers at a smaller rate of taper than over the first longitudinal portion or is constant over the second longitudinal portion; and
the traction feature is disposed distally of the first longitudinal portion.

20. The method of claim 16, wherein:
the tissue processing unit comprises a protective processing sleeve and a container apparatus including the processing container, the container apparatus being removably received in the processing sleeve with the bottom of the container apparatus disposed inside of and toward a bottom of the processing sleeve and with the processing sleeve having an open top not blocking access to the top of the processing container;
during the rotating, the tissue processing unit is in contact with the digestion drive unit only through surfaces of the processing sleeve and no portion of the container apparatus contacts any portion of the digestion drive unit; and
the top portion of the tissue processing unit extending beyond the distal end of the at least one rotational drive member comprises a top portion of the container apparatus that projects beyond the top of the processing sleeve.

* * * * *